(12) United States Patent
Stover

(10) Patent No.: US 9,492,468 B2
(45) Date of Patent: Nov. 15, 2016

(54) METHODS AND COMPOSITIONS FOR TREATMENT OF ACUTE HEART FAILURE

(75) Inventor: Richard R. Stover, West Cornwall, CT (US)

(73) Assignee: PERICOR THERAPEUTICS, INC., New York, NY (US)

(*) Notice: Subject to any disclaimer, the term of this patent is extended or adjusted under 35 U.S.C. 154(b) by 721 days.

(21) Appl. No.: 12/573,043

(22) Filed: Oct. 2, 2009

(65) Prior Publication Data

US 2010/0087500 A1     Apr. 8, 2010

Related U.S. Application Data

(60) Provisional application No. 61/102,769, filed on Oct. 3, 2008.

(51) Int. Cl.
A61K 31/7056 (2006.01)

(52) U.S. Cl.
CPC .................. A61K 31/7056 (2013.01)

(58) Field of Classification Search
None
See application file for complete search history.

(56) References Cited

U.S. PATENT DOCUMENTS

| | | | |
|---|---|---|---|
| 3,586,604 | A | 6/1971 | Yamanoi et al. |
| 4,211,771 | A | 7/1980 | Witkowski et al. |
| 4,432,990 | A | 2/1984 | Robinson |
| 4,575,498 | A | 3/1986 | Holmes et al. |
| 4,912,092 | A | 3/1990 | Gruber |
| 5,008,251 | A | 4/1991 | Gruber |
| 5,030,623 | A | 7/1991 | Gruber |
| 5,082,829 | A | 1/1992 | Gruber et al. |
| 5,118,601 | A | 6/1992 | Gruber |
| 5,132,291 | A | 7/1992 | Gruber |
| 5,187,162 | A | 2/1993 | Marangos et al. |
| 5,200,525 | A | 4/1993 | Gruber et al. |
| 5,366,960 | A | 11/1994 | Gallagher |
| 5,629,298 | A | 5/1997 | Dobson, Jr. |
| 5,646,128 | A | 7/1997 | Firestein et al. |
| 5,658,889 | A | 8/1997 | Gruber et al. |
| 5,731,432 | A | 3/1998 | Erion et al. |
| 5,777,100 | A | 7/1998 | Bullough et al. |
| 5,817,640 | A | 10/1998 | Gruber et al. |
| 6,103,702 | A | 8/2000 | Law |
| 6,221,851 | B1 | 4/2001 | Feldman |
| 2001/0018443 | A1 | 8/2001 | Varney et al. |
| 2003/0092668 | A1* | 5/2003 | Liang et al. .......... 514/46 |
| 2004/0072138 | A1 | 4/2004 | Singh |
| 2005/0002943 | A1 | 1/2005 | Leo et al. |
| 2005/0233987 | A1 | 10/2005 | Lopez Blanco et al. |
| 2006/0253159 | A1* | 11/2006 | Siejko et al. ............ 607/17 |
| 2006/0293273 | A1* | 12/2006 | Mangano .............. 514/45 |
| 2007/0082859 | A1 | 4/2007 | Stover et al. |

FOREIGN PATENT DOCUMENTS

| | | |
|---|---|---|
| EP | 0535884 A1 | 4/1993 |
| EP | 0262125 | 3/1996 |
| EP | 0301900 | 3/1996 |
| EP | 0495091 | 11/1999 |
| GB | 2430882 | 4/2007 |
| WO | WO 9202213 A | 2/1992 |
| WO | WO 9202214 | 2/1992 |
| WO | WO 9926657 A1 | 6/1999 |
| WO | WO 03037371 A2 | 5/2003 |
| WO | WO 03037371 A3 | 10/2004 |
| WO | WO 2006105167 A2 | 10/2006 |
| WO | WO-2007/044357 | 4/2007 |
| WO | WO 2006105167 A3 | 5/2007 |
| WO | WO-2008/055711 | 5/2008 |
| WO | WO 2008086341 A | 7/2008 |
| WO | WO 2009094593 A | 7/2009 |

OTHER PUBLICATIONS

Felker et al., The problem of decompensated heart failure: Nomenclature, classification, and risk stratification, 2003, Am Heart J, vol. 145, pp. 518-525.*
Pollesello et al. "The Cardioprotective Effects of Levosimendan: Preclinical and Clinical Evidence", 2007, J Cardiovasc Pharmacol, vol. 50, No. 3, pp. 257-263.*
Australian Application AU2006230242 Office Action received Oct. 26, 2011.
EP Application 06739900 Office Action dated Aug. 10, 2011.
Galinanes, et al. (1995), "Protection Against Injury During Ischemia and Reperfusion by Acadesine Derivatives GP-1-468 and GP-1-668 Studies in the transplanted rat heart", J. Thorac. Cardiovasc. Surg. (1995) vol. 110, n. 3, p. 752-761.
Indonesian Application WO0200703134 Office Action explanation dated Oct. 3, 2011.
U.S. Appl. No. 11/277,739 Final Rejection mailed Jan. 9, 2012.
Henry, et al. Adenosine Release from Red Cells Mediates Inhibition of Platelet Aggregation by Acadesine and Delays Post-Thrombolytic Reocclusion in Dogs. Circ Suppl. 1991;84:247.
Mazur, et al. Acadesine Preserves Cardiac Function and Enhances Coronary Blood Flow in Isolated, Blood Perfused Rabbit Hearts with Repeated Ischemia and Reperfusion. J. Mol. Cell Cardial. 1991;23:S45.
Mullane, et al. Acadesine: prototype adenosine regulating agent for treating myocardial ischemia-reperfusion injury. Drug Dev Res. 1993; 28:336-343. (Abstract).
Val, et al. Diagnostic Criteria and Prognosis of Perioperative Myocardial Infarction Following Coronary Bypass. J Thorac Cardiovas Surg. 1983; 86:878-886.(Abstract).
Vinten-Johansen, et al. Acadesine Improves Surgical Myocardial Protection with Blood Cardioplegia in Ischemically Injured Canine Hearts. Circulation. 1993; 88:350-358. (Abstract).
Whitehead, et al. A general parmetric approach to the meta-analysis of randomized clinical trials. Stat Med. 1991; 10:1665-1677.

(Continued)

*Primary Examiner* — James D Anderson
*Assistant Examiner* — Meghan Finn
(74) *Attorney, Agent, or Firm* — Morrison & Foerster LLP

(57) ABSTRACT

The present disclosure provides methods and compositions for treating acute heart failure, by administering to a subject in need thereof a therapeutically effective amount of an AICA riboside analog or a pharmaceutically acceptable salt or prodrug thereof.

33 Claims, 5 Drawing Sheets

(56) References Cited

OTHER PUBLICATIONS

MX Application MX/a/2007/012045 Office Action dated May 4, 2011.
Mullane, K. The Prototype Adenosine Regulating Agent for Reducing Myocardial Ischemic Injury. Cardiovasc Res. 1993; 27:43-47.
Aggarwal, et al. K-MB release after coronary artery bypass graft surgery in a multicenter population. Anesthesiology. 1994;81: A1291.(Abstract).
Ambrosio, et al. Effects of ATP Precursors on ATP and free ADP content and functional recovery of post-ischemic hearts. Am. J. Physiol. 1989;256:H560-H566. (Abstract).
American Society of Anesthesiologiests Inc., "Effects of Acadesine on the Incidence of Myocardial Infarction and Adverse Cardiac Outcomes after Coronary Artery Bypass Graft Surgery" Multicenter Study of Perioperative Ischemia (McSPI) Research Group, Anesthesiology, vol. 83, No. 4, Oct. 1995, p. 658-673.
Antman, et al. A comparison of results of meta-analyses of randomized control trials and recommendations of clinical experts: treatments for myocardial infarction. JAMA. 1992; 268:240-248.
Barankiewicz, et al. Alteration of purine metabolism by AICA-riboside in human B lymphoblasts. Arch Biochem Biophys. 1990;282(2):377-385.
Barankiewicz, et al. Selective Adenosine Release from Human B but no T Lymphoid Cell Line. J. Biol. Chem. 1990;265(26):15738-15743.
CASS Principal Investigators and Their Associates. Myocardial Infarction and Mortality in the Coronary Artery Surgery Study (CASS) randomized trial. N. Engl. J. Med. 1984; 310:750-758. (Abstract).
Clark, R. E. Calculating Riak and Outcome: the Society of Thoracic Surgeons database. Ann Thorac Surg. 1996; 62:52-5 (Abstract).
Cronstein, et al. Methotrexate Inhibits Neutrophil Function by Stimulating Adenosine Release from Connective Tissue Cells. Proc Natl Acad Sci USA. 1991;2441-2445.
Demeyere, et al. Cardioprotective effects of acadesine in patients with unstable angina undergoing aortocoronary Bypass Surgery. Circulation. 1994; 90(4, pt 2):1-370. (Abstract).
Dersimonian, et al. Meta-analysis in clinical trials. Control Clin Trials. 1986; 7:177-188.
Dixon, et al. AICA-Riboside: Safety, Tolerance, and Pharmacokinetics of a Novel Adenosine-Regulating Agent. J Clin Pahrmacol. 1991;31: 342-347.
Drew, et al. "Acadesine, an adenosine-regulating agent with the potential for widespread indications" Expert Opin. Pharmacother. (2008) vol. 9, No. 12, p. 2137-2144.
Dyck, et al. "AMPK alterations in cardiac physiology and pathology: enemy or ally?" J. Physiol. (2006) 574.1, p. 95-112.
Egger, et al. Misleading meta-analysis: lessons from an effective, safe, simple intervention that wasn't. BMJ. 1995; 310:752-754. (Abstract).
Ely, et al. Protective Effects of Adenosine in Myocardial Ischemia. Circulation. 1992; 85:893-904 (Abstract).
EP Extended European Search Report for EP06739900.6; dated Jul. 15, 2009; 9 pages.
Galinanes, et al. Acadesine and Myocardial Protection: Studies of Time of Administration and Dose-Response Relations in the Rat. Circulation. 1992;86:598-608. (Abstract).
Gotzsche, P. C. Reference Bias in Reports of Doing Trials. BMJ. 1987; 295:654-656. (Abstract).
Greenberg, G. R. Preparation of 5'-Phosphoribosyl-5-Amino-4-Imidazolecarboxamide. J. Biol. Chem. 1956;219:426-433.
Groziak, et al. Nonenzymatic Synthesis of 5-Aminoimidazole Ribonucleoside and Recognition of its Facile Rearrangements. Proc. Natl. Acad. Sci. USA. Oct. 1988;85:7174-7176.
Gruber, et al. Increased Adenosine concentration in Blood from Ischemic Myocardium by AICA riboside: effects on flow, granulocytes, and injury. Circulation. 1989; 80:1400-1411.
Haraphongse, et al. The Changing Clinical Profile of Coronary Artery Bypass Graft Patients, 1970-1989. Can J. Cardiol. 1994:10:71-86. (Abstract).

Hardie, D. Grahme "AMP-activated protein kinase: the guardian of cardiac energy status" Journal of Clinical Investigation, vol. 114, No. 4, Aug. 2004, p. 465-468.
Hechinger, J. The Growing Case for Heart Surgery. The Wall Street Journal online. 2005. 3 pages.
Hsu, et al. Increased Creatine Kinase-MB and Troponin T. Concentrations and Mortality in CABG Patient, Population Science. 2000; Abstracts 4159.
Ivanovics, et al. The Synthesis of 2-Substituted Derivatives of 5-Amino-I-, beta,-D- Robofuranosylimidazole-4-carboxamide. Ring Opening Reactions of 2-Azapurine Nucleoies. J. Org. Chem. 1974;39(25):4 pages.
Jain, et al. Incidence of Q wave myocardial Infarction During Coronary Artery Bypass Graft Surgery in the 24-Center McSPI Population. Anesthesiology. 1994; 81:A157.
Jeng, et al. A Comparison of Meta-Analytic Results Using Literature vs Individual Patient Data: Paternal Cell Immunization for Recurrent Miscarriage. JAMA. 1995; 274:830-836. (Abstract).
Jones, et al. Coronary Bypass Surgery: is the operation different today? J. Thorac Cardiovasc Surg. 1991; 101:108-115 (Abstract).
Kikugawa, et al. Platelet Aggregation Inhibitors. Chem. Pharm. Bull. 1977;25(8):1959-1969.
Kouchoukos, et al. Report of the Ad Hoc Committee on Risk Factors for Coronary Artery Bypass Surgery. Ann Thorac Surg. 1988; 45:348-349. (Abstract).
Kurz, et al. "Cardioprotection with a novel adenosine regulating agent mediated by intravascular adenosine" European Journal of Pharmacology 322 (1997) 211-220.
Lachin, J. Sample Size Determination for RXC Coimparative Trials. Biometrics. 1977; 331:315-324. (Abstract).
Lau, et al. Cumulative meta-Analysis of Therapeutic Trials for Myocardial Infarction. N Engl J Med. 1992; 327:248-254. (Abstract).
Lee et al. (Abstracts of Papers, 229th ACS National Meeting, San Diego, CA, United States, Mar. 13-17, 2005, MEDI-244. American Chemical Society: Washington, D.C. (Abstract Sent).
Leung, et al. An Initial MultiCenter Randomized Controlled Trial on the Safety and Efficacy of Acadesine in Patients Undergoing CABG Surgery. Anesth Analg. 1994; 78:420-434.
Loh, E. Common Variant in AMPD1 Gene Predicts Improved Clinical Outcome in Patients with Heart Failure. Circulation. 1999;99:1422-1425.
Mangano Jama: "Effects of Acadesine on Myocardial Infarction, Stroke, and Death Following Surgery, A Meta-Analysis of the 5 International Randomized Trials." The Journal of the American Medical Association, Jan. 22-29, 1997, vol. 277, No. 4, p. 325-332 (Abstract sent).
Mangano, D. T. Myocardial Stunning: an overview. J. Cardiac Surg. 1993; 8:204-213. (Abstract).
Mangano, D. T. Perioperative Cardiac Morbidity. Anesthesiology. 1990; 72:153-184.
Mangano, D. T. Perioperative Cardiac Morbidity: Epidemiology, Costs, Problems, and Solutions. West J. Med. 1994; 161:87-89.
Mangano, et al. Association of Perioperative Myocardial Ischemia with Cardiac Morbidity and Mortality in Men Undergoing Noncardiac Surgery. N. Engl. J. Med. 1990; 323:1781-1788.
Mangano, et al. "Post-Reperfusion Myocardial Infarction: Long-Term Survival Improvement Using Adenosine Regulation With Acadesine" Journal of the American College of Cardiology, vol. 48, No. 1, 2006, p. 207-214.
Martin, et al. Prospective, Randomized Trial of Retrograde Warm-Blood Cardioplegia: Myocardial Benefit and Neurologic Threat. Ann Thorac Surg. 1994; 57:298-304. (Abstract).
Marumoto, et al. Synthesis and Coronary Vasodilating Activity of 2-Substituted Adenosines, Chem. Pharm. Bull. 1975;23(4):75-774.
Matsumoto, et al. Adenine Nucleotide Degradation during Energy Depletion in Human Lymphoblasts. J. Biol. Chem. Sep. 10, 1979;254(17):8956-8962.
Menasche, et al. Acadesine: a new drug that may improve myocardial protection in coronary artery bypass graft surgery: results of the first international multicenter study. J. Thorac Cardiovasc Surg. 1995; 110:1096-1106.

(56) References Cited

OTHER PUBLICATIONS

Mentzer, et al. The Acute Effects of AICAR on Purine Nucleotide Metabolism and Postischemic Cardiac Function. J Thorac Cardiovas Surg. 1988; 95-286-293. (Abstract).
Mitsos, et al. Protective effects of AICAriboside in the globally Ischemic Isolated Cat Heart. Pharmacology. 1985; 31(3):121-131. (Abstract only).
Molina-Viamonte, et al. AICA-riboside suppresses Arrhythmias Induced by Coronary Artery Occlusion and Reperfusion. Circulation. 1990; 82:645.
Mullane, K. The Prototype Adenosine Regulating Agent for Reducing Myocardial Ischemic Injury. Cardiovasc Res. 1993; 27:43-47. (Abstract).
Murakami, et al. Synthesis of 2-Formyladenoise Using Diethoxyacetonitrile as a Synthon. Heterocycles. 1981;16(8): 1315-1319.
Murphy, et al. Treatment of Chronic Stable Angina: a Preliminary Report of Survival Data of the Randomized Veterans Administration Cooperative Study. N. Engl. J. Med. 1977;297:621-627. (Abstract).
Novak, et al. Evaluation of the Interaction of Acadesine (ACA) and Allopurinol (Allo). Clinical Pharmacology & Therapeutics. 1993;53(2):161.
Omura, et al. Synthesis of 2-Phenylaminoadenosine from Imidazole Nucleosides. Chem. Pharm. Bull. 1981;29(27):1870-1875.
Oxman, et al. From Science to Practice: Meta-Analyses using Individual Patient Data are needed. JAMA, 1995; 274:845-846.
PCT/US09/059454 International Search Report and Written Opinion mailed Dec. 2, 2009.
Rashid, et al. A Prospective Randomized Study of Continuous Warm Versus Intermittent Cold Blood Cardioplegia for Coronary Artery Surgery: Preliminary Report. Eur J. Cardiothorac Surg. 1994; 8:265-269. (Abstract).
Schaff, et al. Detrimental effect of Perioperative Myocardial Infarction on Late Survival After Coronary Artery Bypass; report from the Coronary Artery Surgery Study (CASS). J Thorac Cardiovasc Surg. 1984; 88:972-981. (Abstract).
Shaw, E. 5-Amino-4-Imidazolecarboxamide Riboside from Inosine. Ring-opeing Reactions of Purine Nucleosides. Organic and Biological Chemistry. Aug. 5, 1958;80:3899-3902.
Shaw, et al. Purines, pyrimidines, and imidazoles. Part 50. Inhibition of adenylosuccinate AMP-lyase No. 4.3.2.2. By derivatives of N-(5-amino-1-beta-D-ribofuranosylimidazole-4-carbonyl)-L-aspartic acid 5'phosphate (SAICAR) and virazole 5'-phosphate. J Chem Soc [Perkin 1]. 1979;6:1415-1424.
Smith, et al. ACC/AHA Guidelines for Percutaneous Coronary Intervention (Revision of the 1993 PTCA Guidelines). Journal of the American College of Cardiology. 2001;(37)8:2239i-22391 xvi.
Smits, et al. Cardioprotective Effects of the Novel Adenosine A1/A2 Receptor Agonist AMP 579 in a Porcine Model of Myocardial Infarction. The Journal of Pharmacology and Experimental Therapeutics. 1998;286:611-618.
Suggs, et al. Synthesis and Biodistribution of p-Iodophenyl Analogues of a Naturally occuring Imidazole Ribonucleoside. J. Heterocyclic Chem. Sep.-Oct. 1988;25(5):1331-1335.
Thacker, S. B. Meta-Analysis: a quantitative Approach to Research Integration. JAMA. 1988; 259: 16851689. (Abstract).
The Multicenter Study of Perioperative Ischemia (McSPI) Research Group. Effects of acadesine on morbidity and mortality following coronary Artery Bypass Graft Surgery. Anesthesiology. 1995; 88:658-673.
The Warm Heart Investigators. Randomized Trial of Normothermic Versus Hypothermic Coronary Bypass Surgery, Lancet. 1994; 343:559-563. (Abstract).
U.S. Appl. No. 11/277,739 Non-Final Rejection mailed Apr. 6, 2007.
U.S. Appl. No. 11/277,739 Non-Final Rejection mailed Feb. 3, 2009.
Varnauskas, E. European Coronary Surgery Study. Z Kardiol. 1985; 6:73-78. (Abstract).

Young, et al. Inhibitiion of Intracoronary Thrombosis by Acadesine: an adenosine-mediated, erythrocyte-dependent activity. Eur Heart J. 1993;14:31.
Young, et al. Progressive Cardiac Dysfunction with Repeated Pacing-Induced Ischemia: Protection by AICA-Riboside. Am J. Physiol. 1991; 261:H1570-H1577. (Abstract).
Yusuf, et al. Magnesium in Acute Myocardial Infarction. BMJ. 1995; 310:751-752. (Abstract).
Yusuf,e t al. Beta Blockade During and After Myocardial Infarction: An Overview of the Randomized Trials. Prog Cardiovasc Dis. 1985; 27:335-371. (Abstract).
EP Application EP06739900 Office Action Aug. 5, 2010.
Ferreira, et al., Jan. 1989, Rev Port Cardiol., v. 8, n. 1, p. 19-26.
G Linanes, et al., 1992, (Abstract)"Acadesine and Myocardial Protection: Studies of Time of Administration and Dose-Response Relations in the Rat", Circulation., v. 86, p. 598-608.
MX Application MX/a/2007/012045 Office Action Sep. 15, 2010.
MX Application MX/a/2007/012045 Office Action Nov. 18, 2010.
Multicenter Study of Perioperative Ischemia (McSI) Researc Group, Anesthesiology, Oct. 1995, v. 83, n. 4, p. 658-673.
New Zealand Application 561649 Office Action Aug. 21, 2009.
New Zealand Application 561649 Office Action Sep. 28, 2010.
PCT/US06/011422 International Search Report Jan. 29, 2007.
PCT/US06/011422 IPRP and Written Opinion.
Philippine Application 12007502139 Office Action dated Feb. 14, 2011.
Srivastava, et al. 1975, "Synthesis of 5-Amino-1-(5-deoxy-beta.-D-Ribofuranosyl) Imidazole-4-Carboxamide and Related 5'-Deoxyimidazole Ribonucleosides", Journal of Medicinal Chemistry, v. 18, n. 12, p. 1237-1240.
U.S. Appl. No. 11/277,739 Non-Final Rejection mailed Feb. 27, 2008.
U.S. Appl. No. 11/277,739 Final Rejection mailed Oct. 5, 2009.
U.S. Appl. No. 11/277,739 Non-Final Rejection mailed Apr. 5, 2011.
Allen and O'Connor, "Management of acute decompensated heart failure," Can. Med. Assoc. J. 176(6):797-805 (2007).
Damasceno et al., "The Causes, Treatment, and Outcome of Acute Heart Failure in 1006 Africans From 9 Countries: Results of the Sub-Saharan Africa Survey of Heart Failure," Arch. Intern. Med. 9 pages, Pubmed abstract (Sep. 2012).
Gheorghiade et al., "Acute Heart Failure Syndromes: Current State and Framework for Future Research," Circulation 112:3958-3968 (2005).
Nieminen et al., "Executive summary of the guidelines on the diagnosis and treatment of acute heart failure," Eur. Heart J. 26:384-416 (2005).
Heart Failure Society of America, "Section 12: Evaluation and Management of Patients with Acute Decompensated Hearty Failure," J. Cardiac Failure 16(6):e134-e156 (2010).
Notice of Reasons for Rejection (with translation) for JP 2011-530281, mailed Dec. 25, 2013, 5 pages.
Engler, R.L., "Harnessing Nature's Own Cardiac Defense Mechanism with Acadesine, an Adenosine Regulating Agent: Importance of the Endothelium," *J. Card. Surg.* 1994, 9(Suppl), 482-492.
Feldman, A.M. et al., "AMPD1 Gene Mutation in Congestive Heart Failure," *Circulation* 1999, 99, 1397-1399.
Funaya, H. et al., "Plasma Adenosine Levels Increase in Patients with Chronic Heart Failure," *Circulation* 1997, 95, 1363-1365 (online version).
Hale, S.L. and R.A. Kloner, "Cardioprotection with Adenosine-Regulating Agent, GP531: Effects on No-Reflow, Infarct Size, and Blood Flow Following Ischemia/Reperfusion in the Rabbit," *J. Cardiovasc. Pharmacol. Ther.* 2010, 15(1), 60-67.
Ingwall, J.S. and W. Shen, "The Chemistry of ATP in the Failing Heart—The Fundamentals," *Heart Failure Rev.* 1999, 4, 221-228.
Ingwall, J. and S. Neubauer, "Prologue," *Heart Failure Rev.* 1999, 4, 209.
Ingwall, J.S. and R.G. Weiss, "Is the Failing Heart Energy Starved? On Using Chemical Energy to Support Cardiac Function," *Circ. Res.* 2004, 95, 135-145.
Ingwall, J.S., "Energy Metabolism in Heart Failure and Remodelling," *Cardiovasc. Res.* 2009, 81, 412-419.

(56) References Cited

OTHER PUBLICATIONS

Jessup, M. et al., "2009 Focused Update: ACCF/AHA Guidelines for the Diagnosis and Management of Heart Failure in Adults," *Circulation* 2009, 119, 1977-2016.

Neubauer, S., "The Failing Heart—An Engine Out of Fuel," *N. Engl. J. Med.* 2007, 356, 1140-1151.

Rosca, M.G. et al., "Cardiac Mitochondria in Heart Failure: Decrease in Respirasomes and Oxidative Phosphorylation," *Cardiovasc. Res.* 2008, 80, 30-39.

Sabbah, H.N. et al., "A Canine Model of Chronic Heart Failure Produced by Multiple Sequential Coronary Microembolizations," *Am. J. Physiol.* 1991, 260, H1379-H1384.

Sabbah, H.N. et al., "Intravenous GP531, an Adenosine Regulating Agent, Improves Left Ventricular Function in Dogs with Chronic Advanced Heart Failure," Poster presented at Heart Failure Congress 2009, Nice, France, May 2009.

Sabbah, H.N. et al., "Intravenous GP531, an Adenosine Regulating Agent, Improves Left Ventricular Function in Dogs with Chronic Advanced Heart Failure," Posted presented at ACC Annual Meeting, Mar. 2010.

Wang, M. et al., "Acute Intravenous Infusion of an Adenosine Regulating Agent Improves Left Ventricular Function in Dogs with Advanced Heart Failure," *Cardiovasc. Drugs Ther.*, 2013, 27(6), 489-498, published online Aug. 2, 2013.

* cited by examiner

METHODS AND COMPOSITIONS FOR TREATMENT OF ACUTE HEART FAILURE

RELATED APPLICATION

This application claims priority to U.S. Provisional Application No. 61/102,769, filed Oct. 3, 2008, the contents of which are hereby incorporated in their entirety by reference.

BACKGROUND

Heart failure represents the final common pathway of many risk factors and cardiovascular illnesses resulting in significant morbidity and mortality. The increase in heart failure rates throughout the world represents an enormous public health problem.

The number of cases and deaths attributable to heart failure has increased despite advances in treatment and a decline in other major cardiovascular diseases over the same interval. Currently more than 5.2 million patients in the United States have heart failure, and more than 550,000 are diagnosed annually. Heart failure leads to 12 to 15 million office visits and 6.5 million hospital days, and more than 57,000 patients die of heart failure as a primary cause annually.

Heart failure is primarily a condition of the elderly, and thus the widely recognized "aging of the population" also contributes to the increasing incidence of heart failure. The incidence of heart failure approaches 10 per 1000 population after age 65, and approximately 80% of patients hospitalized with heart failure are more than 65 years old. Heart failure is the most common Medicare diagnosis-related group (i.e., hospital discharge diagnosis), and more Medicare dollars are spent for the diagnosis and treatment of heart failure than for any other diagnosis. In addition, patients suffering from chronic congestive heart failure have a five-year mortality rate of approximately 50%.

Chronic congestive heart failure is characterized by a progressive loss in the heart's ability to pump blood. Different diseases can cause congestive heart failure, including coronary artery disease, heart attacks, inflammation of the heart tissue and diseases of the heart valves, and infection. Weakened heart muscle often results in poor cardiac output because the heart is unable to empty blood adequately from the ventricles to the circulation with each beat. Congestive heart failure symptoms include shortness of breath, edema, or fluid retention, and swelling of the legs and feet. Congestive heart failure symptoms that result from the inefficiency of the heart to distribute or adequately pump oxygen-rich blood to body tissues include fatigue and weakness as well as a loss of appetite. As the disease progresses, these symptoms can severely impact the patient's quality of life, so that even the ability to perform simple tasks, such as walking across the room, becomes limited. While some cardiac risk factors such as smoking, high cholesterol, high blood pressure, diabetes and obesity can be controlled with lifestyle changes, the majority of patients with CHF require additional treatments to help manage their disease.

Congestive heart failure is characterized as a syndrome rather than a disease, because of the complexity of its many causes and pathophysiological origins. For this reason, current medications for the treatment of CHF are sub-optimal; they include diuretics, inotropes, vasodilators and beta blockers, which generally focus on single components of the diverse pathways contributing to CHF. Diuretics help the kidneys rid the body of excess fluid, thereby reducing blood volume and the heart's workload. Inotropes strengthen the heart's pumping action. Vasodilators, such as ACE inhibitors, cause the peripheral arteries to dilate, making it easier for blood to flow. Beta blockers slow the heart rate and reduce blood pressure by blocking the effects of adrenaline.

Many congestive heart failure patients eventually experience a rapid deterioration and worsening of symptoms, or decompensation, despite continuing medical therapy and require urgent treatment in the hospital. This condition is called acute decompensated heart failure (ADHF or acute heart failure). The number of hospitalizations for worsening congestive heart failure have risen dramatically in the past 30 years from approximately 400,000 in 1979 to approximately 1.1 million in 2005. Acute heart failure is also the most frequent cause of hospitalization among Medicare patients.

Acutely decompensated heart failure resulting in hospitalization marks a fundamental change in the natural history of the progression of congestive heart failure. Reasons for this are unclear but may involve the intensification of existing pathophysiologic processes or entirely new ones, or it may reflect a deleterious effect of conventional treatments given to control worsening symptoms. Mortality rates in the year following hospitalization for acute heart failure patients are significantly higher than in non-hospitalized patients, and heart failure hospitalization remains one of the most important risk factors for mortality. Moreover, these patients are particularly prone to readmission, with recurrent hospitalization rates of 50% within 6 months of discharge.

Treatment strategies for ADHF have been largely empirical and limited by the complex pathophysiology of the syndrome which is not completely understood. Moreover, treatment strategies are complicated by the heterogeneity of clinical presentation among ADHF patients. Traditionally, heart failure has been associated with a reduced left ventricular ejection fraction (generally LVEF <35%) that defines patients with systolic dysfunction. However, over the past decade, there has been a growing recognition of a significant and growing group of acute heart failure patients with preserved LV ejection fraction characterized by diastolic dysfunction. This group of ADHF patients are believed to represent nearly one-half of all ADHF patients. A high proportion of patients with preserved LV ejection fraction are women and diabetics.

Standard treatment regimens for ADHF include diuretics, vasodilators, and inotropic agents to improve symptoms, but no treatment has been shown to improve outcomes (mortality and rehospitalization) of these patients. In fact, in some instances these therapies have been shown to worsen prognosis. Inotropic agents, for example, improve systolic function, as demonstrated by improving left ventricular ejection fraction, but do so by making the damaged heart work harder, as evidenced by increasing myocardial oxygen demand ($MVO_2$), thereby contributing to worsening long-term outcomes.

SUMMARY

The present application discloses treatments of ADHF that improve outcomes for patients. Without being bound by theory it is believed that treatment with AICA riboside analogs, including but not limited to GP-531 (5-amino-1-β-D-(5-benzylamino-5-deoxy-1-β-D-ribofuranosyl)imidazole-4 carboxamide) or a pharmaceutically acceptable salt or prodrug thereof, address the cellular energetics of the heart and its microcirculation. Treatment with AICA riboside analogs addresses the needs of the entire spectrum of ADHF patients and improves outcomes not only for patients with reduced left ventricular ejection fraction but also for patients with preserved left ventricular ejection fraction.

In particular, the present application is generally directed to the use of an AICA riboside analog or a pharmaceutically acceptable salt or prodrug thereof in the treatment of acute heart failure.

In one aspect, the present application is directed to a method for treating acute heart failure comprising administering to a patient in need thereof an AICA riboside analog of Formula I:

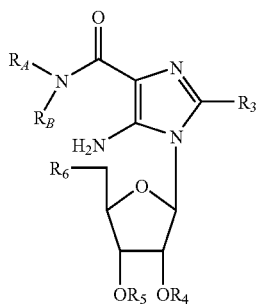

Formula I or a pharmaceutically acceptable salt or prodrug thereof, wherein: $R_A$ is selected from the group consisting of hydrogen, optionally substituted aryl, optionally substituted lower alkyl, optionally substituted aralkyl, optionally substituted cycloalkyl or optionally substituted bicycloalkyl; $R_B$ is hydrogen or optionally substituted lower alkyl; $R_3$ is hydrogen or —SW, where W is hydrogen, optionally substituted lower alkyl, or optionally substituted phenyl; $R_4$ and $R_5$ are independently hydrogen, optionally substituted lower alkyl, or acyl; $R_6$ is hydrogen, hydroxy, phosphate ester, —OSO$_2$NH, halogen, —OCOV, —SV, —SOV, —N$_3$, or —NVV' wherein V and V' are independently selected from hydrogen, optionally substituted aryl, optionally substituted lower alkyl, and optionally substituted —CH$_2$-phenyl; provided that when $R_A$, $R_B$, and $R_3$ are hydrogen, and $R_4$ and $R_5$ are hydrogen, acyl or hydrocarboxycarbonyl, then $R_6$ is not any one of hydroxy, acyloxy or hydrocarbyloxycarboxy.

In another aspect, the present application is directed to a method of increasing the time from a hospital discharge to rehospitalization for an acute heart failure patient comprising administering to said patient an AICA riboside analog of Formula I or a pharmaceutically acceptable salt or prodrug thereof.

In another aspect, the present application is directed to a method for improving the global cardiac function of the heart in an acute heart failure patient, the method comprising administering to said patient an AICA riboside analog of Formula I or a pharmaceutically acceptable salt or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1:
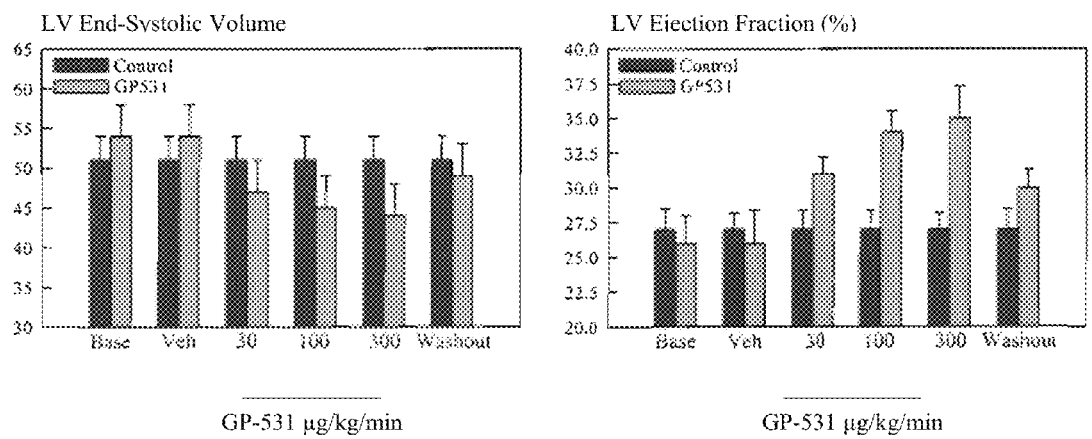
FIG. 1 is a bar graph of Left Ventricular (LV) End-systolic volume (ESV in mL) and LV ejection fraction (LVEF in %) illustrating that subjects in Group I (administered GP-531 tartrate salt at 30 μg/kg/min, 100 μg/kg/min or 300 μg/kg/min) have a significant decrease in ESV and an increase in LVEF in a dose dependent manner.

The heart requires substantial quantities of chemical energy in the form of adenosine triphosphate (ATP) to support its systolic and diastolic mechanical functions. Failure to produce enough cardiac energy causes a mechanical failure of the heart. Elevated levels of endogenous adenosine, a key ATP metabolite, have been identified in patients with heart failure suggesting ongoing net-ATP catabolism in heart failure. Net ATP catabolism generally occurs under conditions of cellular stress caused by stimuli that include but is not limited to oxygen deprivation (e.g. tissue hypoxia), immune activation, neurohormonal activation and inflammation.

Adenosine is often referred to as a 'retaliatory metabolite'—it acts as an endogenous cardioprotective substance that addresses multiple pathways of cellular stress conditions that trigger net ATP catabolism. Endogenous adenosine is a natural protective agent in settings of ischemia cytotoxic injury and in heart failure. Adenosine is present in small quantities in the normal myocardium, and is transiently increased during episodes of cellular stress by sequential degradation of high-energy phosphates (ATP, ADP, and AMP). ATP catabolism results in the production of adenosine and inosine in the course of rapid cellular energy utilization, such as during seizure activity, arrhythmias, or a condition caused by decreased blood flow, such as stroke or heart attack.

The physiological tissue levels of adenosine are regulated by the production and release of adenosine by cardiac myocytes, the endothelium, neutrophils and other cell types. Adenosine interacts with specific G-protein coupled purinergic (adenosinergic) receptors on the endothelium, myocytes or neutrophils to elicit a wide range of physiological responses not unlike those of nitric oxide (NO). The physiologic effect resulting from activation of the specific adenosinergic receptor is typically transduced by either stimulating adenylate cyclase ($G_s$) and increasing cAMP levels ($A_2$ receptors) or inhibiting adenylate cyclase (Gi) and decreasing cAMP levels ($A_1$ and $A_3$ receptors). The physiologically diverse effects of adenosine are related to the differential effects on the G-protein coupled receptors and post-receptor effectors such as $K_{ATP}$ channels, protein kinase C (PKC) activity, phosphatidylinositol-3 (PI-3) kinase, nitric oxide synthase, potassium channels, and sodium-hydrogen exchange (NHE) systems to name a few. Therefore, adenosine exerts a broad spectrum of effects on key components (neutrophils, endothelium) and compartments (intravascular, interstitial, myocyte) involved in cardiac injury.

Adenosine is also a potent inhibitor of neutrophil functions. Hence, the cooperative activation between platelets and neutrophils, leading to amplified activation that causes cellular stress to myocytes and endothelial cells may be attenuated by endogenous adenosine. Prolonged coronary occlusion followed by reperfusion produces necrosis within the area at risk, beginning in the subendocardium and extending with occlusion time toward the subepicardium in a wavefront pattern. Previous studies have suggested adenosine could (a) reduce infarct size on a long term basis (inhibition versus delay) when adenosine is administered at the onset of reperfusion, thereby identifying the reperfusion period as a feasible therapeutic time point, (b) inhibit neutrophil accumulation in the area at risk, or at least attenuate plugging of the capillaries, (c) reduce endothelial damage, and (d) attenuate the complex processes of reperfusion injury leading to contractile dysfunction.

In heart failure, endogenous adenosine release, such as occurs during the degradation of ATP, is generally insufficient to overcome the varied stimuli of cellular stress and improve the mechanical function of the heart.

One approach to improving the mechanical function of the heart of a heart failure patient is to supplement endogenous adenosine levels, with the goal of improving cardiac energy metabolism. Another approach is to improve cardiac energy metabolism by preserving or increasing ATP.

One method of increasing extracellular adenosine concentration or preserving or increasing ATP is administration of a therapeutically effective amount of an agent which increases extracellular adenosine, including an adenosine regulating agent ("ARA"). Adenosine regulating agents are involved in the inhibition of adenosine catabolism and enhancement of adenosine tissue concentration. Administration of adenosine regulating agents, such as, for example, acadesine (5-amino-4-imidazole carboxamide riboside, AICA riboside), enhances adenosine tissue concentrations, which in turn improves microcirculatory function and reduces myocardial injury. ARAs enhance the local concentrations of endogenous adenosine only under conditions of ATP catabolism and are pharmacologically silent in tissues undergoing normal ATP metabolism; ARAs have been shown not to alter hemodynamics. Although acadesine is a purine nucleoside analog, its pathway of metabolism is via inosine monophosphate (IMP) ultimately to uric acid; one side effect of administration of acadesine is the unwanted buildup of uric acid and crystalluria at higher or prolonged dosing.

DEFINITIONS

Unless specifically noted otherwise herein, the definitions of the terms used are standard definitions used in the art of organic synthesis and pharmaceutical sciences.

As used herein "heart failure" refers to a condition that occurs when a problem with the structure or function of the heart impairs its ability to supply sufficient blood flow to meet the body's needs.

The term "chronic heart failure" as used herein means a case of heart failure that progresses so slowly that various compensatory mechanisms work to bring the disease into equilibrium.

"Acute heart failure" or "acute chronic heart failure" as used herein refers to both sudden onset heart failure, as well as acute "exacerbated" or "decompensated" heart failure ("ADHF"), referring to episodes in which a patient with known chronic heart failure abruptly develops worsening symptoms and requires hospitalization. Thus, an acute heart failure patient includes a patient with chronic heart failure who experiences a deterioration and worsening of symptoms despite continuing medical therapy and requires hospitalization, as well as a hospitalized patient who has not previously been diagnosed with acute heart failure (i.e. hospitalized with sudden onset heart failure). There are no treatments that have been shown to improve outcomes, e.g. post-discharge mortality or rehospitalization, for acute heart failure patients and some treatments to alleviate symptoms are believed to worsen prognosis. After hospitalization, acute heart failure patients have a different prognosis compared to chronic heart failure patients, and so for purposes of this discussion, even after discharge from the hospital, heart failure patients are considered 'acute heart failure' patients, although they might not require immediate hospitalization. Common symptoms of complications due to acute heart failure include, but are not limited to, dyspnea due to pulmonary congestion or cardiogenic shock due to low cardiac output, easy fatigueability (exercise intolerance), peripheral edema, anasarca (pronounced generalized edema), nocturia (frequent nighttime urination), bradycardia, heart block, hypotension, dizziness, syncope, diabetes, oliguria or anuria, hypokalemia, bronchospasm, cold sweat, and asthma.

A "cardiovascular event" as used herein refers to myocardial infarction, unstable angina, cardiac thrombus, resuscitated cardiac arrest, or cardiac death.

"Left Ventricular Ejection Fraction" ("LVEF") refers to a measure of systolic function of the left ventricle. The ejection fraction is the percentage of blood ejected from the left ventricle with each heart beat. An LVEF of 50% indicates that the left ventricle ejects half its volume each time it contracts. In some patients, a normal LVEF is 50% or higher; generally a LVEF >40% is considered a 'preserved ejection fraction.' A reduced LVEF, for example, less than or equal to about 35% indicates that cardiomyopathy is present.

The phrase "LV mechanical efficiency" is a measure of how efficiently the left ventricle works as a pump. Efficiency in this context is a product of the energy utilized by the heart for pumping and is quantified as myocardial oxygen consumption and LV power generation i.e. the power with which the LV ejects its blood content during systole.

The phrase "global cardiac function" as used herein refers to the overall function of the heart as a whole, e.g. the efficacy and efficiency with which the heart pumps blood. Global LV function refers to the overall function of the left ventricle. In all cases, overall function implies both systolic function as well as diastolic function. Hemodynamic assessments of LV systolic function include LVEF, cardiac output, stroke volume, fractional area of shortening, as well as left ventricular end-diastolic and end-systolic volumes. LV diastolic function can be assessed by measurements of LV end-diastolic pressure, mitral valve velocity E/A and Ei/Ai ratios, and mitral inflow E wave deceleration time.

"Diastolic dysfunction" refers to an abnormality in the heart's (i.e., left ventricle's) filling during diastole. Diastole is the phase of the cardiac cycle when the heart (i.e. ventricle) is not contracting but is relaxed and filling with blood that is being returned to it (either from the body (into right ventricle) or from the lungs (into left ventricle)). Typically, diastolic dysfunction denotes a stiffer ventricular wall, which leads to inadequate filling of the ventricle, and therefore an inadequate stroke volume. The failure of ventricular relaxation also results in elevated end-diastolic pressures. Diastolic dysfunction may not manifest itself except in physiologic extremes if systolic function is preserved. The patient may be completely asymptomatic at rest, but is extremely sensitive to increases in heart rate and sudden bouts of tachycardia.

"Systolic dysfunction" refers to an abnormality in the heart's (i.e., left ventricle's) ability to pump blood out of the chamber into the systemic circulation. Systole is a phase of the cardiac cycle where the myocardium is contracting in a coordinated manner in response to an endogenous electrical stimulus, and pressure is being generated within the chambers of the heart driving blood flow. Experimental and clinical measurement of systolic contraction are often based on ejection fraction and cardiac output.

The term "treatment" is used herein refers to amelioration or reduction of a symptom or a condition affecting an organism, such as a mammal, including but not limited to, humans.

Insofar as the methods of the present invention are directed to preventing diseases, it is understood that the term "prevent" does not require that the disease state be completely thwarted. Rather, as used herein, the term preventing refers to the ability of the skilled artisan to identify a person or population that is susceptible to a disease, such that administration of the compounds of the present invention may occur prior to onset of that disease. The term does not imply that the disease state be completely avoided.

The term "alkyl" refers to saturated aliphatic groups, including straight, branched and carbocyclic groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to alkyl groups that are cyclic groups of 3 to 6 or 3 to 10 atoms. Suitable cyclic groups include norbornyl and cyclopropyl. Such groups may be substituted.

The term "bicycloalkyl", refers to two cyclic alkyl groups fused together, each ring having between 5-8 carbon atoms.

The term "aryl" refers to aromatic groups having from about 6 to 14 carbon atoms and includes cyclic aromatic systems such as phenyl and naphthyl.

The term "aralkyl" refers to an alkyl group of about 1 to 4 carbon atoms substituted with an aryl group of from 6 to 10 carbon atoms and includes, for example, benzyl, p-chlorobenzyl, p-methylbenzyl and 2-phenylethyl.

The term "lower hydrocarbyl" refers to an organic radical comprised of primarily 1 to 10 carbon atoms and hydrogen and includes alkyl, alkenyl and alkynyl groups, as well as aromatic groups including aryl and aralkyl groups and groups which have a mixture of saturated and unsaturated bonds, alicyclic (carbocyclic or cycloalkyl) groups or such groups substituted with aryl (aromatic) groups or combinations thereof and may refer to straight-chain, branched-chain or cyclic structures or to radicals having a combination thereof.

The term "halo" or "halogen" refers to fluorine, chlorine, bromine and iodine.

The term "acyl" refers to the group —C(O)R', wherein R' is lower hydrocarbyl.

The term "acyloxy" refers to the ester group —O—C(O)R', wherein R' is lower hydrocarbyl The term "phosphate ester" refers to the group

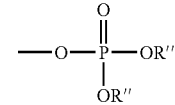

wherein R" is independently hydrogen or lower hydrocarbyl and/or to compounds having at least one such group, and includes salts thereof.

The term "hydrocarbyloxycarbonyl" refers to the group R'—O—C(O)— wherein R' is lower hydrocarbyl.

The term "hydrocarbyloxycarboxy" refers to the group R'—O—C(O)—O wherein R' is lower hydrocarbyl.

"Optionally substituted" groups may be substituted or unsubstituted. The substituents of an "optionally substituted" group may include, without limitation, one or more substituents independently selected from the following groups or designated subsets thereof: alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyesters, carboxamido, acyloxy, hydrogen, —F, —Cl, —Br, —I, —CN, —NO$_2$, —NH$_2$, —N$_3$, —NHCH$_3$, —N(CH$_3$)$_2$, —SH, —SCH$_3$, —OH, —OCH$_3$, —OCF$_3$, —CH$_3$, —CF$_3$, —C(O)CH$_3$, —CO$_2$CH$_3$, —CO$_2$H, —C(O)NH$_2$, —OR', —SR' and —NR'R" wherein each of R' and R" is hydrocarbyl. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere between fully substituted and monosubstituted (e.g., —CH$_2$CF$_3$).

AICA riboside analogs that may be used in the compositions and methods disclosed herein include those described in U.S. Pat. No. 5,777,100, which is incorporated herein in its entirety by reference. Exemplary analogs of AICA riboside include compounds of Formula I:

Formula I

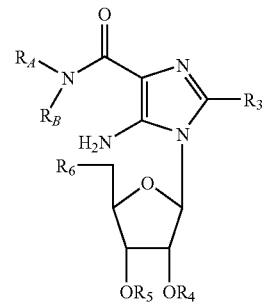

or a pharmaceutically acceptable salt or prodrug thereof, wherein:

R$_A$ is selected from the group consisting of hydrogen, optionally substituted aryl, optionally substituted lower alkyl, optionally substituted aralkyl, optionally substituted cycloalkyl and optionally substituted bicycloalkyl;

R$_B$ is hydrogen or optionally substituted lower alkyl;

R$_3$ is hydrogen or —SW, where W is hydrogen, optionally substituted lower alkyl, or optionally substituted phenyl;

$R_4$ and $R_5$ are independently hydrogen, optionally substituted lower alkyl, or acyl;

$R_6$ is hydrogen, hydroxy, phosphate ester, —OSO$_2$NH, halogen, —OCOV, —SV, —SOV, —N$_3$, or —NVV' wherein V and V' are independently selected from hydrogen, optionally substituted aryl, optionally substituted lower alkyl, and optionally substituted —CH$_2$-phenyl;

provided that when $R_A$, $R_B$, and $R_3$ are hydrogen, and $R_4$ and $R_5$ are hydrogen, acyl or hydrocarboxycarbonyl, then $R_6$ is not any one of hydroxy, acyloxy or hydrocarbyloxycarboxy.

In one embodiment, the compounds include those of Formula I wherein $R_A$ is selected from the group consisting of hydrogen, optionally substituted lower alkyl, optionally substituted aralkyl, or optionally substituted cycloalkyl;

$R_B$, $R_3$, $R_4$ and $R_5$ are each hydrogen;

$R_6$ is hydrogen, hydroxy, —N$_3$, or —NVV' wherein V and V' are independently selected from hydrogen, optionally substituted aryl, optionally substituted lower alkyl, and optionally substituted —CH$_2$-phenyl.

In one variation, $R_A$ is hydrogen, optionally substituted lower alkyl, optionally substituted cycloalkyl, or optionally substituted aralkyl; $R_B$ is hydrogen; and $R_6$ is hydroxy, —NH$_2$ or a phosphate ester.

In another embodiment, the compounds include those of Formula I wherein:

$R_A$, $R_B$, $R_3$, $R_4$ and $R_5$ are each hydrogen;

$R_6$ is —NVV' wherein V and V' are independently selected from hydrogen, optionally substituted aryl, optionally substituted lower alkyl, and optionally substituted —CH$_2$-phenyl.

In one embodiment the compounds useful in the methods disclosed herein include those of Formula I wherein $R_A$ is an optionally substituted aralkyl group, generally an optionally substituted benzyl group, such as a benzyl group having from 1 to 3 ring substitutions, or an optionally substituted cycloalkyl or a pharmaceutically acceptable salt, or prodrug thereof.

In another embodiment the compounds useful in the methods disclosed herein include those of Formula I wherein each of $R_A$ and $R_B$ is hydrogen, $R_6$ is —NVV', where V and V' are independently selected from hydrogen, optionally substituted aryl, optionally substituted lower alkyl, optionally substituted —CH$_2$-phenyl, or a pharmaceutically acceptable salt or prodrug thereof. In one variation V is hydrogen and V' is an optionally substituted aralkyl group, generally an optionally substituted benzyl group.

One typical AICA riboside analog that can be used in the methods disclosed herein is a compound having the chemical structure of Formula II:

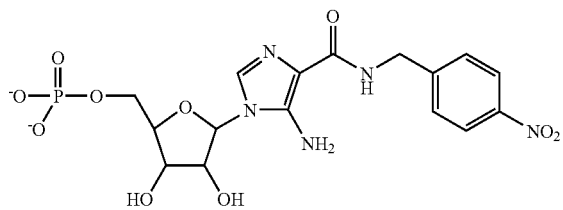

Formula II or a pharmaceutically acceptable salt or prodrug thereof.

Another AICA riboside analog that can be used in the methods disclosed herein is a compound having the chemical structure of Formula III:

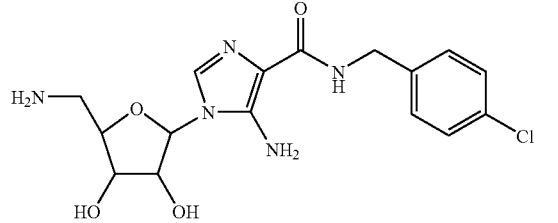

Formula III or a pharmaceutically acceptable salt or prodrug thereof.

Yet another AICA riboside analog that can be used in the methods disclosed herein has the chemical structure of Formula IV:

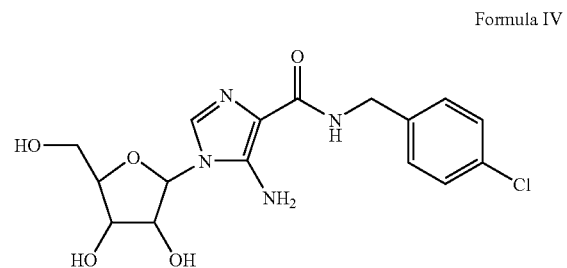 [SMILES: Nc1c(C(=O)NCc2ccc(Cl)cc2)ncn1C1OC(CO)C(O)C1O]

Formula IV or a pharmaceutically acceptable salt or prodrug thereof.

Another AICA riboside analog to be used in the methods disclosed herein is GP-531 having the chemical structure of Formula V:

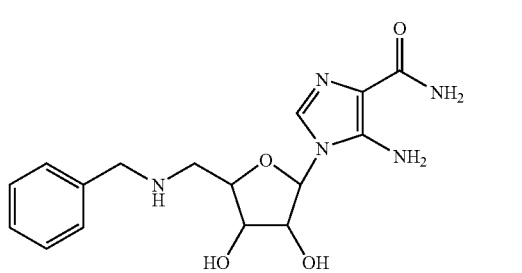

Formula V or a pharmaceutically acceptable salt or prodrug thereof.

Use of salts and prodrugs of AICA riboside analogs are contemplated for the methods described herein, including salts and prodrugs of a compound of Formula V, GP-531. A non-limiting exemplary salt of GP-531 is L-tartrate and a non-limiting exemplary prodrug is a compound of Formula Va:

Formula Va

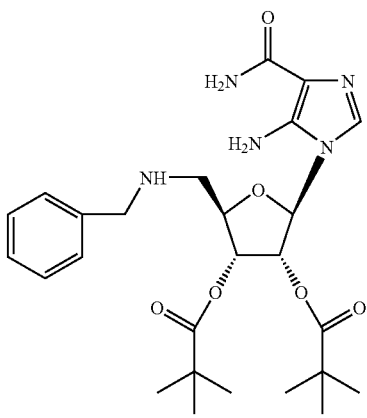

or a pharmaceutically acceptable salt thereof.

Prodrugs of AICA riboside analogs can be prepared according to methods known to those of skill in the art and administered to acute heart failure patients as disclosed herein. In one embodiment, the prodrugs enhance oral bioavailability and include carboxylic acid esters, in particular such prodrugs include di-O-pivaloyl derivatives, such as represented by Formula Va.

AICA riboside analogs also include isomers of the compounds of Formula I; in particular, isomers of Formula II, III, IV and V include, but are not limited to:

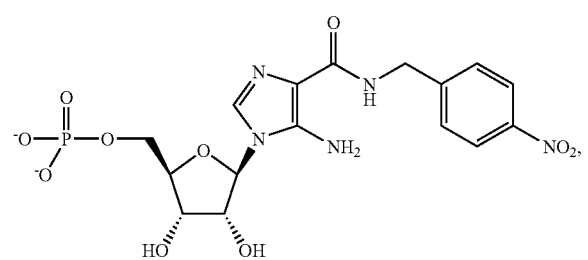

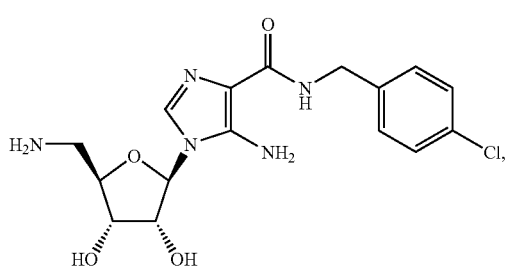

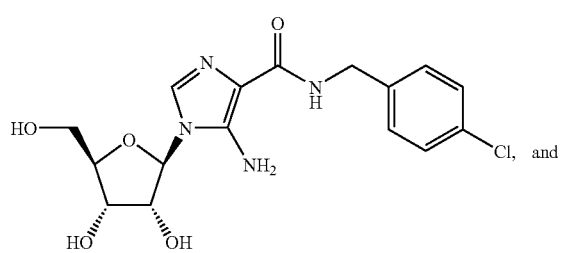

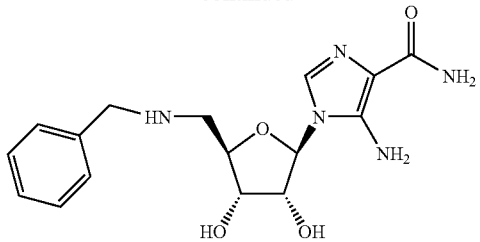

Compounds of Formula I, particularly compounds of Formula II, III, IV and V, are a second generation adenosine regulating agents (ARAs) that increase endogenous adenosine concentrations only in tissues undergoing ATP catabolism, and as such their pharmacologic activity is both event-specific and site-specific. Therapeutic levels of AICA riboside analogs such as Formula II, III, IV and V are pharmacologically silent in normally metabolizing tissues, resulting in no direct cardiac or systemic hemodynamic effects. The effects of ARAB are not mediated by conversion of the drug to adenosine or by any direct activity at the adenosine receptors. GP-531 in particular, has not been shown to be a ligand for A1, A2, or A3 receptors for the NBTI-sensitive adenosine transporter.

A composition comprising an AICA riboside analog, such as a compound of Formula I, or in particular a compound of Formula II, III, IV, or V, or pharmaceutically acceptable salt or prodrug thereof, include but are not limited to acid addition and/or base salts. Pharmaceutically acceptable salts of the compounds may include the acid addition and base salts (including disalts) thereof, such as L-tartrate salt. Examples of suitable salts can be found for example in Stahl and Wermuth, Handbook of Pharmaceutical Salts Properties, Selection, and Use, Wiley-VCH, Weinheim, Germany (2002); and Berge et al., "Pharmaceutical Salts," J. of Pharmaceutical Science, 1977; 66:1-19.

Pharmaceutically acceptable acid addition salts of the compounds described herein include non-toxic salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include the acetate, aspartate, benzoate, besylate (benzenesulfonate), bicarbonate/carbonate, bisulfate, caprylate, camsylate (camphor sulfonate), chlorobenzoate, citrate, edisylate (1,2-ethane disulfonate), dihydrogenphosphate, dinitrobenzoate, esylate (ethane sulfonate), fumarate, gluceptate, gluconate, glucuronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, mesylate (methanesulfonate), metaphosphate, methylbenzoate, methylsulfate, 2-napsylate (2-naphthalene sulfonate), nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, tosylate (toluene sulfonate), and xinafoate salts, and the like of compounds described herein. Also contemplated are the salts of amino acids such as arginate, gluconate, galacturonate, and the like.

Acid addition salts of the basic compounds may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts may be formed with metals or amines, such as alkali and alkaline earth metal hydroxides, or of organic amines. Examples of metals used as cations are aluminum, calcium, magnesium, potassium, sodium, and the like. Examples of suitable amines include arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine), and tromethamine.

The base addition salts of acidic compounds may be prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

In one aspect, the present application is directed to a method for treating acute heart failure comprising administering to a patient in need thereof an AICA riboside analog of Formula I or a pharmaceutically acceptable salt or prodrug thereof, as disclosed herein. In another aspect, the present application is directed to a method for treating acute heart failure comprising administering to a patient in need thereof an AICA riboside analog of Formula I or a pharmaceutically acceptable salt or prodrug thereof as disclosed herein, wherein said patient has a LVEF >35%. Alternately, the heart failure patient has a LVEF >40%. In one embodiment of any aspect disclosed herein, the AICA riboside analog is a compound of Formula II, III, IV or V or a pharmaceutically acceptable salt or prodrug thereof; alternately the AICA riboside analog is a compound of Formula V or a pharmaceutically acceptable salt or a prodrug thereof. In one variation, the analog is GP531 tartrate salt.

In one embodiment, an AICA riboside analog of Formula I, such as Formula II, III, IV or V, in particular a compound of Formula V or a salt or prodrug thereof is administered in an amount effective to provide relief from one or more symptoms of acute heart failure. In one variation, the one or more symptoms is selected from the group consisting of dyspnea, easy fatigueability, and peripheral edema. In another embodiment, an AICA riboside analog of Formula I, such as Formula II, III, IV or V, in particular a compound of Formula V or a salt or prodrug thereof is administered in an amount effective to reduce the need for administration of a diuretic, an inotrope or a vasodilator to the acute heart failure patient. In one embodiment, the amount of a diuretic, an inotrope or a vasodilator required by the acute heart failure patient is reduced; in another embodiment, the dose regimen of a diuretic, an inotrope or a vasodilator is abbreviated.

In another aspect, the present application is directed to a method of increasing the time from a hospital discharge to re-hospitalization for an acute heart failure patient comprising administering to a patient in need thereof an AICA riboside analog of Formula I or a pharmaceutically acceptable salt or prodrug thereof, as disclosed herein. In another aspect, the present application is directed to a method of increasing the time from a hospital discharge to re-hospitalization for an acute heart failure patient comprising administering to a patient in need thereof an AICA riboside analog of Formula I or a pharmaceutically acceptable salt thereof as disclosed herein, wherein said patient has a LVEF >35%. Alternately, the acute heart failure patient has a LVEF >40%. In one embodiment of any of the disclosed aspects, the AICA riboside analog is of Formula II, III, IV or V or a pharmaceutically acceptable salt or prodrug thereof; alternately the AICA riboside analog is of Formula V or a pharmaceutically acceptable salt or prodrug thereof. In one variation, the analog is GP531 tartrate salt. In one variation of any of the disclosed aspects or embodiments, the patient is not rehospitalized for 30 days after hospital discharge. In another variation, the patient is not rehospitalized for 60 days after hospital discharge. In another variation, the patient is not rehospitalized for 90 days after hospital discharge. In yet another variation, the patient is not rehospitalized for 4 months, or even 6 months after a hospital discharge. In one embodiment, the time between a discharge from a second hospitalization and a rehospitalization is increased; in an alternate embodiment, the time between a discharge from a third hospitalization and a rehospitalization is increased. In one variation, the acute heart failure patient has been hospitalized for acute heart failure more than twice. In another variation of any of the disclosed aspects or embodiments, the rehospitalization is due to a cardiovascular event, alternately the rehospitalization is due to heart failure.

In another aspect, the present application is directed to a method for improving the global cardiac function of the heart in an acute heart failure patient, the method comprising administering to a patient in need thereof an AICA riboside analog of Formula I or a pharmaceutically acceptable salt or prodrug thereof, as disclosed herein. In one embodiment, the acute heart failure patient has a LVEF >35%, alternately the heart failure patient has a LVEF >40%. In one embodiment of any of the disclosed aspects, the AICA riboside analog is of Formula II, III, IV or V or a pharmaceutically acceptable salt or prodrug thereof; alternately the AICA riboside analog is of Formula V or a pharmaceutically acceptable salt or prodrug thereof. In one variation, the analog is GP531 tartrate salt. In one variation of any of the disclosed embodiments, the improved global cardiac function is an improved function of the left ventricle. In one embodiment, the improved LV function reflects improvement in LV systolic function, such as one or more of LVEF, cardiac output and stroke volume. In another embodiment, improved LV function reflects improvement in LV diastolic function. In another embodiment, improving the global cardiac function enhances the efficiency of cardiac contraction in the patient without deleterious effects that include hypotension, tachycardia or arrhythmia. In one variation of any disclosed aspect or embodiment, the AICA riboside analog is a compound of Formula V or a pharmaceutically acceptable salt thereof, such as tartrate or a pharmaceutically acceptable prodrug, such as a compound of Formula Va or a salt thereof.

In another aspect, the present application discloses a method of reducing the number of days an acute heart failure patient spends in the hospital for heart failure the method comprising administering to a patient in need thereof an AICA riboside analog of Formula I or a pharmaceutically acceptable salt or prodrug thereof, as disclosed herein. In one embodiment, the acute heart failure patient has a LVEF >35%, alternately the heart failure patient has a LVEF >40%. In one embodiment of any of the disclosed aspects, the AICA riboside analog is of Formula II, III, IV or V or a pharmaceutically acceptable salt or prodrug thereof; alternately the AICA riboside analog is of Formula V or a pharmaceutically acceptable salt or prodrug thereof. In one variation, the analog is GP531 tartrate salt. In one variation of any of the disclosed aspects or variations, the number of days in the hospital is reduced by 10%, alternately by 20% or even by 30% or 40%. Generally, an acute heart failure patient spends between 5 and 6 days in the hospital. Administration of an AICA riboside analog of Formula I, such as Formula II, III, IV or V, in particular a compound of Formula V or its salt or prodrug, reduces the hospital stay of an acute heart failure patient to four days or even three days.

In one variation of any of the aspects or embodiments disclosed herein, the patient has no evidence of a prior myocardial infarction (non-ischemic cardiomyopathy). In another embodiment of any of the aspects disclosed herein, the patient is male; alternately, the patient is female. In yet another embodiment of any of the aspects disclosed herein, the patient is younger than 65; alternately the patient is older than 65. In yet another embodiment of any of the aspects disclosed herein, the acute heart failure patient has a left ventricular ejection fraction that is equal to or greater than 35% or is equal to or greater than 40%; alternately, the heart failure patient has a left ventricular ejection fraction ejection equal to or greater than 50%. In another variation of any aspect or embodiment disclosed herein, the acute heart failure patient has a left ventricular ejection fraction ejection greater than about 35% and the patient has not been diagnosed as having had a myocardial infarction. In one embodiment the heart failure results from an initial non-ischemic inciting influence. In one embodiment, the non-ischemic inciting influence is selected from the group consisting of amyloidosis, cardiomyopathy, hypertension, valvular diseases, infections, toxins or impairment in the nervous stimulation of the heart, anemia, hyperthyroidism, hypothyroidism, cardiac fibrosis and combinations thereof.

In one embodiment of any aspect disclosed herein, the therapeutic agent, e.g. an AICA riboside analog of Formula I, such as Formula II, III, IV or V, in particular a compound of Formula V or its salt or prodrug, is administered at from about 1 µg/kg/min to about 300 µg/kg/min. In one embodiment of any aspect disclosed herein, the therapeutic agent is administered over at least about 24 hours at between about 3 µg/kg/min and about 300 µg/kg/min, or alternately between about 1 µg/kg/min to about 100 µg/kg/min. Generally the therapeutic agent is administered at less than about 100 µg/kg/min, less than about 50 µg/kg/min, less than about 25 µg/kg/min or even less than about 10 µg/kg/min. Alternately, therapeutic agent is administered at about 2 µg/kg/min, about 6 µg/kg/min, about 18 µg/kg/min, about 54 µg/kg/min, or even about 100 µg/kg/min. In particular, the therapeutic agent is GP531 tartrate. Generally, the AICA riboside analog, such as GP531 or its salt or prodrug, is administered for between about 1 hour and about 24 hours. Alternatively, the AICA riboside analog, such as GP531 or its salt or prodrug, is administered for between about 12 hour and about 24 hours or between about 24 and about 48 hours, or between about 24 and about 72 hours. Alternatively, the AICA riboside analog, such as GP531 or its salt or prodrug, is administered for at least about 6 hours, at least about 8 hours, at least about 24 hours, at least about 48 hours or even at least about 96 hours. In one embodiment, an AICA riboside analog of Formula I, II, III, IV or V or a pharmaceutically acceptable salt or prodrug thereof is administered at about 4 mg/kg to about 450 mg/kg. In another embodiment, a compound of Formula V or a pharmaceutically acceptable salt or prodrug thereof is administered in an amount of from about 4 mg/kg to about 450 mg/kg; in one variation, the analog is a tartrate salt of the compound of Formula V; in another variation, the analog is a compound of Formula Va or a salt thereof, such as a hydrochloride salt. In yet another embodiment, an AICA riboside analog of Formula I, II, III, IV or V or a pharmaceutically acceptable salt or prodrug thereof is administered in an amount of from about 1 mg/kg to about 250 mg/kg. In another embodiment, a compound of Formula V or a pharmaceutically acceptable salt or prodrug thereof is administered in an amount of about 1 mg/kg to about 250 mg/kg; in one variation, the analog is a tartrate salt of the compound of Formula V; in another variation, the analog is a compound of Formula Va or a salt thereof, such as a hydrochloride salt. The therapeutic agent can be administered as a intravenous infusion or as an oral dose administered one, two, three or even four times a day. The dose of GP531 L-tartrate salt to an acute heart failure patient in need thereof is generally between about 1.44 mg/kg/day and about 432 mg/kg/day, or alternately between about 1.44 mg/kg/day to about 144 mg/kg/day. Generally the dosage form provides less than about 144 mg/kg/day, less than about 72 mg/kg/day, less than about 36 mg/kg/day or even less than about 14 mg/kg/day. Alternately, the dosage form provides about 3 mg/kg/day, about 9 mg/kg/day, about 26 mg/kg/day, about 78 mg/kg/day, or even about 144 mg/kg/day. Such dosing can be accomplished via intravenous infusion; alternately, the dosing can be via oral administration or other methods known to those of skill in the art, including but not limited to transdermal administration.

In one embodiment of any aspect disclosed herein, an AICA riboside analog intravenous dosage form disclosed herein is administered for at least about 24 hours during a hospital stay and following discharge an AICA riboside intravenous dosage form disclosed herein is administered twice a week, once a week, twice a month or once a month, for example via intravenous infusion over about 4 hours, over about 6 hours or over about 8 hours. Alternately, the dosage form is oral and can be administered as a single dose or as multiple doses over the course of a day. In one variation, the AICA riboside analog is a compound of Formula I or a pharmaceutically acceptable salt or prodrug thereof. Alternately, the compound is of Formula II, III, IV or V, in particular a compound of Formula V or its salt or prodrug. In one variation, a dose of from about 4 mg/kg to about 450 mg/kg or of from about 1 mg/kg to about 250 mg/kg of a tartrate salt of a compound of Formula V is administered as an IV infusion on a first day and, further a dose of from about 4 mg/kg to about 450 mg/kg or of from about 1 mg/kg to about 250 mg/kg of a tartrate salt of a compound of Formula V is administered as an IV infusion on a second day. In another variation, a dose of a prodrug of Formula V is administered orally in an amount equivalent to from about 4 mg/kg to about 450 mg/kg or from about 1 mg/kg to about 250 mg/kg of a tartrate salt of a compound of Formula V on a first day and further, a dose of a prodrug of Formula V is administered orally in an amount equivalent to from about 4 mg/kg to about 450 mg/kg or of from about 1 mg/kg to about 250 mg/kg of a tartrate salt of a compound of Formula V on a second day. Generally, the second dose is administered the day after administration of the first dose, alternately, the second dose is administered two days after administration of the first dose, or three days, four days, five days, six days or even seven days after administration of the first dose. In one embodiment, the first dose is administered over at least about 12 hours and the second dose is administered over at least about 6 hours, or at least about 8 hours, at least about 12 hours or even over at least about 24 hours.

When an alternate AICA riboside analog is administered, such as, for example a compound of Formula I, or a compound of Formula II, III, or IV, or a salt of the compound of Formula V other than tartrate, or pharmaceutically acceptable salt or prodrug thereof, a therapeutic dose equivalent to the dose described above for GP531 tartrate can be calculated based on the drug's molecular weight.

Generally, administering to an acute heart failure patient an AICA riboside analog of Formula I, such as Formula II, III, IV or V, in particular Formula V or a pharmaceutically acceptable salt or prodrug thereof accomplishes one or more of:

(a) increasing the number of days after discharge from a hospitalization that the acute heart failure patient is alive and out of the hospital;

(b) prolonging the time to rehospitalization of an acute heart failure patient, such as rehospitalization due to heart failure or a cardiovascular event;

(c) reducing the number of days a patient spends in the hospital for acute heart failure, such as for example reducing a stay from 5 or 6 days to 4 days or to 3 days;

(d) reducing the total number of days a patient spends in the hospital for heart failure for two or more hospital stays;

(e) reducing the number of hospital admissions for heart failure;

(f) reducing mortality due to heart failure;

(g) increasing left ventricular ejection fraction in an acute heart failure patient;

(h) improving the quality of life in an acute heart failure patient based on the Kansas City Cardiomyopathy Questionnaire, or the Minnesota Living with Heart Failure questionnaire;

(i) decreasing levels of B-type natriuretic peptide (j) decreasing levels of cardiac troponin; and (k) reducing cardiomegaly in a patient in need thereof.

The present invention provides methods and compositions for treating cardiac conditions, in particular acute heart failure, wherein the acute heart failure patient has either a reduced LVEF or a preserved LVEF. Cardiac conditions generally affect a large number of individuals, for example, chronic cardiac disease is a leading cause of mortality and morbidity in the developed world; heart disease is a leading cause of death in the United States and acute myocardial infarction (AMI) typically results from a thrombus that obstructs blood flow in one or more coronary arteries and is a common and life-threatening complication of coronary heart disease. Heart failure may include acute heart failure (including cardiogenic shock) or congestive heart failure, such as caused by a cardiomyopathy, which may be a dilative, restrictive, or hypertrophic cardiomyopathy. As discussed herein, acute heart failure patients require hospitalization for treatment of heart failure symptoms.

Administration

It will be understood that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the heart failure, as is well understood by those skilled in the art. Convenient dosing of AICA riboside analogs of Formula I, such as Formula II, III, IV and V in humans is available for chronic use in acute heart failure patients having a reduced LVEF, as well as patients having a preserved LVEF. Such dosing includes, but is not limited to, a once a day or twice a day administration, such as a tablet or capsule, as well as intravenous infusions. The use of time-release preparations to control the rate of release of the active ingredient as well as continuous infusions may also be employed. The dose may be administered in as many divided doses as is convenient.

Unit dosage formulations can be those containing a daily dose or unit, daily sub-dose, or an appropriate fraction thereof, of an AICA riboside analog, such as a compound of Formula I or a pharmaceutically acceptable salt or prodrug thereof, or in particular, of Formula II, III, IV, or V, or pharmaceutically acceptable salt or prodrug thereof, such as GP531 tartrate, or a prodrug of Formula Va or a salt thereof. The unit dose may be for oral consumption, such as by a tablet or capsule, or for infusion, or administered by other means as disclosed herein. In some embodiments, the dose amount is provided once a day, twice a day, 3 times a day, or 4 or more times a day. In other embodiments, the dose amount is provided twice a week, once a week, twice a month or once a month. For example, a dose of from about 200 µg/kg to about 100 mg/kg, or from about 360 µg/kg to about 36 mg/kg, or from about 360 µg/kg to about 3.6 mg/kg can be provided twice a day, 3 times a day, or 4 or more times a day. In some embodiments, such a dose is provided twice a week, once a week, twice a month or once a month. The amount may be provided by oral consumption, infusion, or administered by other means familiar to those of skill in the art, such as transdermal or transmucosal.

In other embodiments, the unit dose may provided as an infusion, wherein the unit dose is administered at from about 3 to about 300 µg/kg/min. For example, the compositions described herein can be administered intravenously, such as by an IV drip using IV solutions well known in the art (e.g., isotonic saline (0.9% NaCl) or dextrose solution (e.g., 5% dextrose), optionally the intravenous solution further includes preservatives, e.g. sodium metabisulfite. For example, a dose of from about 3 to about 300 µg/kg/min can be provided by infusion, such as by IV drip once a day, twice a week, once a week, twice a month or once a month. Alternately, the unit dose is infused once a day, twice a day, 3 times a day, or 4 or more times a day, for a period of time.

In other embodiments, the unit dose is from about 1 to about 500 mg/kg, about 1 to about 450 mg/kg, about 1 to about 400 mg/kg, about 1 to about 350 mg/kg, about 1 to about 300 mg/kg, about 1 to about 250 mg/kg, about 1 to about 200 mg/kg, about 1 to about 150 mg/kg, about 1 to about 100 mg/kg, about 1 to about 50 mg/kg, about 1 to about 25 mg/kg, about 1 to about 20 mg/kg, about 1 to about 15 mg/kg, about 1 to about 10 mg/kg, about 1 to about 5 mg/kg, about 2 to about 500 mg/kg, about 2 to about 450 mg/kg, about 2 to about 400 mg/kg, about 2 to about 350 mg/kg, about 2 to about 300 mg/kg, about 2 to about 250 mg/kg, about 2 to about 200 mg/kg, about 2 to about 150 mg/kg, about 2 to about 100 mg/kg, about 2 to about 50 mg/kg, about 2 to about 25 mg/kg, about 2 to about 20 mg/kg, about 2 to about 15 mg/kg, about 2 to about 10 mg/kg, about 2 to about 5 mg/kg, 3 to about 500 mg/kg, about 3 to about 450 mg/kg, about 3 to about 400 mg/kg, about 3 to about 350 mg/kg, about 3 to about 300 mg/kg, about 3 to about 250 mg/kg, about 3 to about 200 mg/kg, about 3 to about 150 mg/kg, about 3 to about 100 mg/kg, about 3 to about 50 mg/kg, about 3 to about 25 mg/kg, about 3 to about 20 mg/kg, about 3 to about 15 mg/kg, about 3 to about 10 mg/kg, or about 3 to about 5 mg/kg of an AICA riboside analog, such as a compound of Formula I, or in particular, of Formula II, III, IV, or V, or pharmaceutically acceptable salt or prodrug thereof. In general the unit dose comprises a compound of Formula V, or a pharmaceutically acceptable salt thereof, such as tartrate salt, or a prodrug thereof, such as a compound of Formula Va or a salt thereof.

In some embodiments, the unit dose is at least about 2 μg/kg, 5 μg/kg, 10 μg/kg, 15 μg/kg, 20 μg/kg, 30 μg/kg, 40 μg/kg, 50 μg/kg, 60 μg/kg, 70 μg/kg, 80 μg/kg, 90 μg/kg, 100 μg/kg, 150 μg/kg, 200 μg/kg, 250 μg/kg, 300 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1 mg/kg, 2 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 250 mg/kg, 300 mg/kg, 350 mg/kg. 400 mg/kg, 450 mg/kg, 500 mg/kg or more of an AICA riboside analog, such as a compound of Formula I, or in particular, of Formula II, III, IV, or V, or pharmaceutically acceptable salt or prodrug thereof. In general the unit dose comprises a compound of Formula V, or a pharmaceutically acceptable salt thereof, such as L-tartrate salt, or a prodrug thereof, such as a compound of Formula Va or a salt thereof.

In other embodiments, an AICA riboside analog, such as a compound of Formula I, or in particular, of Formula II, III, IV, or V or pharmaceutically acceptable salt or prodrug thereof, is provided at a unit dose from about 2 to about 500 μg/kg/min, 2 to about 400 μg/kg/min, 2 to about 300 μg/kg/min, 2 to about 200 μg/kg/min, 2 to about 100 μg/kg/min, 2 to about 75 μg/kg/min, 2 to about 50 μg/kg/min, 2 to about 25 μg/kg/min, 2 to about 10 μg/kg/min, 2 to about 5 μg/kg/min, 2 to about 3 μg/kg/min, 3 to about 500 μg/kg/min, 3 to about 400 μg/kg/min, 3 to about 300 μg/kg/min, 3 to about 100 μg/kg/min, 3 to about 200 μg/kg/min, 3 to about 50 μg/kg/min, 3 to about 25 μg/kg/min, 3 to about 10 μg/kg/min, or 3 to about 5 μg/kg/min. In other embodiments, at least about 2 μg/kg/min, about 3 μg/kg/min, about 4 μg/kg/min, about 5 μg/kg/min, about 6 μg/kg/min, about 7 μg/kg/min, about 8 μg/kg/min, about 9 μg/kg/min, about 10 μg/kg/min, about 15 μg/kg/min, about 20 μg/kg/min, about 25 μg/kg/min, about 30 μg/kg/min, about 35 μg/kg/min, about 40 μg/kg/min, about 45 μg/kg/min, about 50 μg/kg/min, about 55 μg/kg/min, about 60 μg/kg/min, about 65 μg/kg/min, about 70 μg/kg/min, about 75 μg/kg/min, about 80 μg/kg/min, about 85 μg/kg/min, about 90 μg/kg/min, about 95 μg/kg/min, about 100 μg/kg/min, about 110 μg/kg/min, about 120 μg/kg/min, about 130 μg/kg/min, about 140 μg/kg/min, about 150 μg/kg/min, about 160 μg/kg/min, about 170 μg/kg/min, about 180 μg/kg/min, about 190 μg/kg/min, about 200 μg/kg/min, about 225 μg/kg/min, about 250 μg/kg/min, about 275 μg/kg/min, about 300 μg/kg/min, about 350 μg/kg/min, about 400 μg/kg/min, about 450 μg/kg/min, about 500 μg/kg/min, about 550 μg/kg/min, about 600 μg/kg/min, about 650 μg/kg/min, about 700 μg/kg/min or more is provided by a unit dose.

The effective amount of an AICA riboside analog, such as a compound of Formula I, or in particular, of Formula II, III, IV, or V, or pharmaceutically acceptable salt or prodrug thereof, in particular a compound of Formula V, or a pharmaceutically acceptable salt thereof, such as L-tartrate salt, or a prodrug thereof, such as a compound of Formula Va or a salt thereof, can be provided for at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 120 hours, or more. In some embodiments, the dose is provided for about 1 hour to about 72 hours, about 1 hour to about 48 hours, or about 1 hour to about 12 hours. Alternately, the analog can be provided for about 4 hours to about 12 hours, about 12 to about 24 hours or about 6 hours to about 8 hours.

The administration of an AICA riboside analog, such as a compound of Formula I, or in particular, of Formula II, III, IV, or V, or pharmaceutically acceptable salt or prodrug thereof, can also be in escalating doses. For example, a first dose of an AICA riboside analog, such as a compound of Formula I, or in particular, of Formula II, III, IV, or V, or pharmaceutically acceptable salt or prodrug thereof, is administered and a second dose administered is greater than the first dose. Additional doses may be given, such as a third dose, such that the third dose greater than the second dose. The doses may be of the same or different AICA riboside analogs, for example, a first dose may be of Formula V, and the second of Formula IV. Alternatively, the first and second dose may both be of Formula V, or a salt thereof, such as tartrate salt.

In some embodiments, a bolus comprising an AICA riboside analog, such as a compound of Formula I, or in particular, of Formula II, III, IV, or V, or pharmaceutically acceptable salt or prodrug thereof, generally GP-531 or a pharmaceutically acceptable salt or prodrug thereof (such as GP-531 tartrate); and a pharmaceutical composition comprising an AICA riboside analog, such as a compound of Formula I, or in particular, of Formula II, III, IV, or V, or pharmaceutically acceptable salt or prodrug thereof, generally GP-531 or a pharmaceutically acceptable salt or prodrug thereof (such as GP-531 tartrate) are administered to a subject with acute heart failure, for a period of time sufficient to treat said acute heart failure. In one variation, the pharmaceutical composition is administered subsequent to administration of the bolus. The bolus can be in an amount from between about 70 μg/kg to about 700 μg/kg; the subsequent administration is generally at from about 3 μg/kg/min to about 300 μg/kg/min according to the ranges disclosed herein.

The pharmaceutically composition comprising AICA riboside analog, such as a compound of Formula I, or in particular, of Formula II, III, IV, or V, or pharmaceutically acceptable salt or prodrug thereof, administered following the bolus may be the same or different as the bolus. For example, the bolus may be of Formula V, and the AICA riboside analog provided for a period of time after the initial bolus may be of a compound of Formula IV. Alternately, the bolus and the compound provided following the bolus are both a compound of Formula V, or a pharmaceutically acceptable salt or prodrug thereof.

Combination Therapy

The preventive or therapeutic compositions of the present invention can also be used in combination with conventional therapeutics of heart failure such as diuretics, inotropes, coronary vasodilators and beta blockers or conventional therapeutics of circulatory diseases such as hypertension (e.g. angiotensin converting enzyme (ACE) inhibitors, angiotensin receptor blockers (ARBs) and/or calcium channel blockers), either simultaneously or at different times. Diuretics are generally used for relief of congestive symptoms and help the kidneys rid the body of excess fluid, thereby reducing blood volume and the heart's workload. Diuretics can include, but are not limited to loop diuretics (e.g. furosemide, bumetanide); thiazide diuretics (e.g. hydrochlorothiazide, chlorthalidone, chlorthiazide); potassium-sparing diuretics (e.g. amiloride); spironolactone and eplerenone. Inotropes, such as a cardiac glycoside, a beta-adrenergic agonist or a phosphodiesterase inhibitor, strengthen the heart's pumping action in patients with low cardiac output; inotropes can include but are not limited to digoxin, dobutamine, milrinone, istaroxime, omecamtiv mecarbil. Vasodilators, cause the peripheral arteries to dilate, making it easier for blood to flow; examples of vasodilators include, but are not limited, nitroglycerin, nitorprusside, and neseritide. Activation of neurohormonal systems that include the renin-andiotensin-aldosterone system (RAAS) and the sympathetic nervous system also contribute to the pathophysiology of heart failure. Drugs that inhibit activation of RAAS fall into three major categories: ACE inhibitors (including but not limited to ramipril, enalapril, and captopril), ARBs (including but not limited to valsarten, candesarten, irbesarten and losarten), and aldosterone receptor blockers (e.g., spironolactone and eplerenone.) Beta blockers counter the effects of activation of the sympathetic nervous system and slow the heart rate by blocking the effects of adrenalin; beta blockers include, but are not limited to carvedilol, metoprolol, bisoprolol, atenolol, propranolol, timolol and bucindolol.

Formulations

For the purposes of this application, the AICA riboside analogs, such as e.g. a compound of Formula I, or in particular, of Formula II, III, IV, or V, or pharmaceutically acceptable salt or prodrug thereof may be administered by a variety of means including orally, parenterally, by inhalation spray, topically, or rectally in formulations containing pharmaceutically acceptable carriers, adjuvants and vehicles. The AICA riboside analogs can also be administered as depot formulations. Pharmaceutical compositions containing the active ingredient may be in any form suitable for the intended method of administration.

The term parenteral as used herein includes subcutaneous, intravenous, intramuscular, and intraarterial injections with a variety of infusion techniques. Intraarterial and intravenous injection as used herein includes administration through catheters.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the application contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the application suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the application may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the application may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The compositions can be administered intravenously or by catheter-based techniques, or a combination thereof, with or without associated delivery devices (i.e. pumps). For example, treatment can be administered intravenously, in or associated with cardioplegia solutions, via local delivery procedures including direct injection into grafts or native arteries, and via perfusion-assisted techniques. The compositions of the present invention can be infused intravenously, while other therapeutically active agents are delivered to the target organ selectively, or both therapies can be delivered by either intravenous or intravascular selective administration.

As noted above, formulations of the present application suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

The compositions described herein can be immediate-release formulations. A variety of known methods and materials may be used to bring about the immediate release. For instance, placement of the agent along an exterior of a tablet (e.g., coating the exterior or formulating the outer layer with the agent) and/or combined with forming a tablet by compressing the powder using low compaction can produce immediate-release of the agent from the composition. The composition can also be in a controlled-release form. The compositions can also be in a sustained release form.

The compositions therefore can comprise one or more carriers that protect the agents against rapid elimination from the body, such as time-release formulations or coatings. Such carriers include controlled-release formulations, including, for example, microencapsulated delivery systems. Compounds of Formula I, or in particular, of Formula II, III, IV, or V or a pharmaceutically acceptable salt or prodrug thereof, can be included in the pharmaceutically acceptable carrier in amounts sufficient to treat an individual. The controlled-release form can be in an amount that is effective to protect the agent from rapid elimination from the body, or to provide a sustained release or dosage, such as between about 1 µg/kg/min to about 300 µg/kg/min, or alternately between about 3 µg/kg/min to about 300 µg/kg/min. Generally the dosage form provides less than 100 µg/kg/min, less than 50 µg/kg/min or even less than 10 µg/kg/min.

In certain embodiments the compositions are in oral dosage form and comprise a matrix that includes a controlled-release material. In certain embodiments, the matrix is compressible into a tablet and can be optionally overcoated with a coating that can control the release of the AICA riboside analog, such as a compound of Formula I, or in particular, of Formula II, III, IV, or V, or pharmaceutically acceptable salt or prodrug thereof, from the composition. In this embodiment, AICA riboside analog, such as a compound of Formula I, or in particular, of Formula II, III, IV, or V, or pharmaceutically acceptable salt or prodrug thereof, are maintained within a therapeutic range over an extended period of time. In certain alternate embodiments, the matrix is encapsulated.

Tablets or capsules containing a composition of the present invention can be coated or otherwise compounded to provide a dosage form affording the advantage of prolonged action. For example, the tablet or capsule can contain an inner dosage and an outer dosage component, the latter being in the form of an envelope over the former. The two components can be separated by an enteric layer that serves to resist disintegration in the stomach and permit the inner component to pass intact into the duodenum or to be delayed in release. For controlled extended release, the capsule can also have micro drilled holes.

A coating comprising an initial dose or first dose of AICA riboside analog, such as a compound of Formula I, or in particular, of Formula II, III, IV, or V, or pharmaceutically acceptable salt or prodrug thereof, in immediate release form, can be added to the outside of a controlled-release tablet core comprising a second dose of AICA riboside analog, such as a compound of Formula I, or in particular, of Formula II, III, IV, or V, or pharmaceutically acceptable salt or prodrug thereof, to produce a final dosage form. Such a coating can be prepared by admixing the first dosage with polyvinylpyrrolidone (PVP) 29/32 or hydroxypropyl methylcellulose (HPMC) and water/isopropyl alcohol and triethyl acetate. Such an immediate-release coating can be spray coated onto the tablet cores. The immediate-release coating can also be applied using a press-coating process with a blend consisting of 80% by weight promethazine and 20% by weight of lactose and hydroxypropyl methylcellulose type 2910. Press-coating techniques are known in the art.

The immediate-release or controlled-release dosage forms of the present invention can also take the form of a multi-layer tablet, such as a bi-layered tablet, which comprises a first layer and a second layer. In a further aspect of the bi-layered tablet, the first layer is an immediate release layer and/or the second layer is a controlled-release layer. For example, a multilayered tablet can comprise at least one immediate release layer comprising an amount of a compound of Formula I, or in particular, of Formula II, III, IV, or V, or pharmaceutically acceptable salt or prodrug thereof and at least one controlled release layer which comprises an amount of AICA riboside analog, such as a compound of Formula I, or in particular, of Formula II, III, IV, or V, or a pharmaceutically acceptable salt or prodrug thereof. The controlled release layer may provide sustained release of AICA riboside analog, such as a compound of Formula I, or in particular, of Formula II, III, IV, or V, or pharmaceutically acceptable salt or prodrug thereof, for a period of time. Alternatively, the immediate release layer and the controlled released layer may provide sustained release of AICA riboside analog, such as a compound of Formula I, or in particular, of Formula II, III, IV, or V or pharmaceutically acceptable salt or prodrug thereof, but at different dosage amounts. In one embodiment, the first layer and second layer both comprise a compound of Formula V, or a pharmaceutically acceptable salt or prodrug thereof, such as GP-531 tartrate or a compound of Formula Va or salt thereof.

The immediate-release or controlled release dosage forms of the present invention can also take the form of pharmaceutical particles manufactured by a variety of methods, including but not limited to high-pressure homogenization, wet or dry ball milling, or small particle precipitation. Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size. These dosage forms can include immediate-release particles in combination with controlled-release particles in a ratio sufficient useful for delivering the desired dosages of active agents.

In another aspect of the present invention, the components are released from a multi-layered tablet that comprise at least a first layer, a second layer and a third layer. Wherein, the layers containing a therapeutically active agent can be optionally separated by one or more layers of inert materials. In one embodiment the layers containing an agent have similar rates of release, e.g. all are immediate release or all are controlled-release. In an alternative embodiment the layers have different rates of release. In this aspect at least one layer is an immediate release layer and at least one layer is a controlled release layer.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Transdermal delivery systems manufactured as an adhesive disc or patch that slowly releases the active ingredient for percutaneous absorption may be used. To this end, permeation enhancers may be used to facilitate transdermal penetration of the active agent. For example, for transdermal administration, the compounds herein may be combined with skin penetration enhancers, such as propylene glycol, polyethylene glycol, isopropanol, ethanol, oleic acid, N-methylpyrrolidone, dimethyl sulfoxide, and the like, which increase the permeability of the skin to the compounds, and permit them to penetrate through the skin and into the bloodstream. The compounds herein may also be combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The compounds may be administered transdermally to achieve a local concentration of the active agent or to achieve systemic administration of the active agent.

Generally speaking, transdermal drug delivery systems are commonly either reservoir-type or matrix-type devices. Both types of devices include a backing layer that forms the outer surface of the finished transdermal device and which is exposed to the environment during use, and a release liner or protective layer that forms the inner surface and which covers the adhesive means for affixing the devices to the skin or mucosa of a user. The release liner or protective layer is removed prior to application, exposing the adhesive means which is typically a pressure-sensitive adhesive. The active agent is located between the release liner and backing layer, usually solubilized or dispersed in a solvent or carrier composition. In some embodiments, the outer surface of the transdermal device (e.g., patch) is adapted to associate with a second component, such as a heating compartment (e.g., electrical or chemical means for providing controlled and consistent increase in temperature).

EXAMPLES

Example 1

Animal Models

Studies were performed in purpose-bred, healthy and conditioned mongrel dogs weighing between 20 and 30 kg. The study was approved by Henry Ford Health System Institutional Animal Care and Use Committee and conformed to the National Institute of Health "Guide and Care for Use of Laboratory Animals" and the "Position of the American Heart Association on Research Animal Use" (*Position of the American Heart Association on Research Animal Use. Circulation* 1985; 71; 49A-50A).

Chronic LV dysfunction and failure was produced by multiple sequential intracoronary embolizations with polystyrene Latex; coronary microembolizations were performed during cardiac catheterization under general anesthesia and sterile conditions (Sabbah H N, et al. *Am J Physiol* (1991) 260:H1379-84; Sabbah H N, et al. *Circulation* (1994) 89:2852-9; Sabbah H N, et al. *Am J Cardiol* 99:41 A-46A, (2007)). Anesthesia was induced using a combination of intravenous injections of oxymorphone hydrochloride (0.22 mg/kg) and diazepam (0.2-0.6 mg/kg). Plane of anesthesia was maintained throughout the study using 1% to 2% isoflurane. Left and right heart catheterizations were performed via a femoral arteriotomy and venotomy. Coronary microembolizations were discontinued when LV ejection fraction, determined angiographically, was about 25%. A period of 2 weeks was allowed after the last microembolization to ensure that infarctions produced by the last microembolizations have completely healed and heart failure was established before the study is undertaken.

Example 2

Chronic Left Ventricular (LV) Dysfunction in Dogs with Advanced Heart Failure: A Dose Escalation Study Eight heart failure dogs described in Example 1 were used. Seven of 8 dogs underwent two studies, one with active drug GP-531 tartrate and one with vehicle (placebo) and 1 of 8 dogs underwent only one active drug GP-531 study. The order of active drug and placebo was randomized and performed about one week apart. In 6 of 8 dogs, after baseline hemodynamic, and ventriculographic measurements, vehicle was administered as a continuous intravenous infusion for one hour. At the end of one hour, the active drug GP-531 tartrate was administered in 3 escalating dose of continuous intravenous infusion with each dose maintained for one hour. At the end of the last drug dose, infusion was stopped and a washout period of one hour was instituted. The same infusion rates and times between doses were used when vehicle studies were performed. At the end of each hour, hemodynamic and angiographic measurements were made. Venous blood samples were obtained at baseline and at one hour after each dose. Blood samples (at least 10 mL) were centrifuged at 3000 rpm for 10 minutes and plasma withdrawn and placed in cryostorage tubes and stored upright at −20° C. for future use. In 2 of 8 dogs, active drug was administered as bolus followed by a constant infusion for 3 hours as noted below.

Active drug was used in dog groups as follows:
1. In 3 of 8 dogs, escalating doses of 30, 100 and 300 μg/kg/min GP-531 tartrate were used (Group I)
2. In another 3 of 8 dogs, escalating doses of 3, 10 and 30 μg/kg/min GP-531 tartrate were used (Group II).
3. In 1 of 8 dogs, active drug was administered as 700 μg/kg GP-531 tartrate bolus followed by a constant infusion of 10 μg/kg/min GP-531 tartrate for 3 hours.
4. In another 1 of 8 dogs, two active drug studies were performed. In one study, active drug was administered as 70 μg/kg bolus followed by a constant infusion of 1.0 μg/kg/min for 4 hours and in the second study, active drug was administered as 210 μg/kg bolus followed by a constant infusion of 3.0 μg/kg/min for 4 hours.

Study Primary End-Points were: (1) change in LV ejection fraction determined from ventriculography and (2) change in LV end-systolic and end-diastolic volume determined from ventriculography.

All hemodynamic measurements were made during left and right heart catheterizations in anesthetized dogs at each specified study time point. Heart rate (HR), mean aortic pressure (mAoP), LV end-diastolic pressure (LVEDP), stroke volume (SV), cardiac output (CO) and systemic vascular resistance SVR) were measured at each study time point. Left ventriculograms were performed during cardiac catheterization after completion of the hemodynamic measurements. Left ventriculograms were obtained with the dog placed on its right side and digitally recorded during the injection of 20 ml of contrast material (RENO-M-60 Squibb, Princeton, N.J.). Correction for image magnification was made using a radiopaque grid placed at the level of the LV. LV end-systolic (ESV) and end-diastolic volumes (EDV) were calculated from angiographic silhouettes using the area length method (Dodge H T, et al. *Am J Cardiol*. (1966) 18:10-24). Premature beats and posiextrasystolic beats were excluded from the analysis. LV ejection fraction (EF) were calculated as the ratio of the difference of end-diastolic and end-systolic volumes to end-diastolic volume times 100 (Sabbah H N, et al. *Am J Physiol* (1991) 260:H1379-84; Sabbah H N, et al., *Circulation* (1994) 89:2852-9; Sabbah H N, et al, *Am J Cardiol* 99:41 A-46A, (2007)).

Plasma biomarkers were measured in Groups I and II. Troponin I (TnI) was determined in plasma based on the principle of the double antibody sandwich enzyme-linked immunosorbent assay (ELISA) (Hirano, T., et al., *Immunol Today* 1990, 11:443-449) and n-terminal brain natriuretic peptide (NT-pro-BNP) based on competitive ELISA (Bonow, R. O. *Circulation* 1996, 93:1946-1950). Both biomarkers were assayed using commercially available assay kits. Kits for NT proBNP and TnI were purchased from ALPCO Diagnostics, Salem, N.H. Using standard curves and software, the concentration of each biomarker was expressed as ng/ml for TnI and fmol/ml for NT-proBNP.

Within group hemodynamic and angiographic data were analyzed using repeated measures analysis of variance (ANOVA) with alpha set at 0.05. If the overall ANOVA was significant, then pairwise comparisons between baseline and drug or placebo dose/time point were performed using the Student-Newman-Keuls test. For this test, a p-value of <0.05 was considered significant. All data are reported as the mean±SEM.

Results: None of the dogs entered into the study developed acute decompensation and none died. In addition, none of the dogs developed de-novo, sinus tachycardia or hypotension at anytime during either active drug infusions or vehicle infusion.

Findings in Control Dogs: Seven of 8 dogs entered into the study were also studied during a 3 hours infusion of saline followed by a 1 hour washout period. Saline infusion had no effects on HR, mAoP, LVEDP, SV, CO, and SVR (Table 1). Similarly, saline infusion had no effects on EDV, ESV or EF (Table 1, FIG. 1).

TABLE 1

Hemodynamic and ventriculographic measures during saline (vehicle control) infusion (n = 7).

|  | Baseline | Vehicle | 1 Hour | 2 Hours | 3 Hours | Washout |
|---|---|---|---|---|---|---|
| HR (beats/min) | 83 ± 3 | 86 ± 5 | 84 ± 3 | 84 ± 3 | 81 ± 4 | 89 ± 6 |
| mAoP (mmHg) | 75 ± 4 | 78 ± 4 | 73 ± 3 | 69 ± 3 | 70 ± 2 | 70 ± 3 |
| LVEDP (mmHg) | 15 ± 1 | 15 ± 1 | 14 ± 1 | 14 ± 1 | 15 ± 1 | 14 ± 2 |
| EDV (ml) | 67 ± 3 | 67 ± 3 | 68 ± 3 | 67 ± 3 | 67 ± 3 | 67 ± 3 |
| ESV (ml) | 49 ± 2 | 49 ± 2 | 50 ± 2 | 49 ± 2 | 49 ± 2 | 50 ± 2 |
| EF (ml) | 27 ± 1 | 27 ± 1 | 27 ± 1 | 27 ± 1 | 27 ± 1 | 27 ± 1 |
| SV (ml) | 18 ± 1 | 18 ± 1 | 18 ± 1 | 18 ± 1 | 18 ± 1 | 18 ± 1 |
| CO (L/rain) | 1.50 ± 0.10 | 1.57 ± 0.14 | 1.53 + 0.11 | 1.49 ± 0.12 | 1.48 ± 0.12 | 1.61 ± 0.16 |
| SVR (dynes-sec-cm$^{-5}$) | 4035 ± 131 | 4106 ± 291 | 3877 ± 177 | 3768 ± 151 | 3851 ± 168 | 3610 ± 217 |

\* = p < 0.05 vs. Baseline

Figure 2:
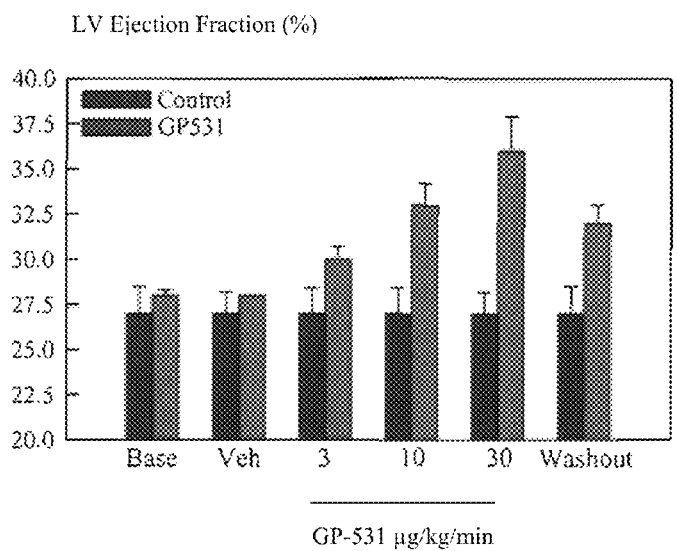
FIG. 2 is a bar graph of LVEF (in %) illustrating that subjects in Group II (administered GP-531 tartrate salt at 3 μg/kg/min, 10 μg/kg/min or 30 μg/kg/min) have an increase in LVEF in a dose dependent manner.

Findings in Group I and Group II Dogs: Group I dogs (n=3) received escalating doses of GP-531 tartrate of 30, 100 and 300 µg/kg/min. In this group, there were no differences between baseline measure and measures obtained during one hour of saline infusion (Vehicle). At these doses, GP-531 tartrate had no effect on HR or mAoP (Table 2). GP-531 tartrate significantly decreased LVEDP. GP-531 tartrate had only a modest and not statistically significant effect on reducing EDV but significantly decreased ESV and increased EF in a dose dependent manner (Table 2, FIG. 1). The observed improvements were associated with a significant increase in SV, CO and a decrease in SVR (Table 2). One hour after discontinuation of GP-531 tartrate infusion, hemodynamic and ventriculographic benefits were attenuated but in many instances remained significantly better than baseline values (Table 2).

no differences between baseline measure and measures obtained during one hour of saline infusion (Vehicle). At these doses, GP-531 tartrate had no effect on HR or mAoP (Table 2) but significantly decreased LVEDP (Table 3). GP-531 tartrate had no effects on EDV but significantly decreased ESV and increased EF in a dose dependent manner (Table 3, FIG. 2). At these doses, GP-531 tartrate modestly increased SV and CO and modestly decreased SVR but none of these changes reached statistical significance compared to baseline (Table 3). One hour after discontinuation of GP-531 tartrate infusion, hemodynamic and ventriculographic benefits were attenuated but in many instances remained significantly better than baseline values

TABLE 2

Hemodynamic and ventriculographic measures during GP-531 tartrate infusion in Group I dogs (n = 3)

|  | Baseline | Vehicle | GP-531 @ 30 µg/kg/min | GP-531 @ 100 µg/kg/min | GP-531 @ 300 µg/kg/min | Washout |
|---|---|---|---|---|---|---|
| HR (beats/min) | 85 ± 2 | 87 ± 5 | 88 ± 9 | 90 ± 9 | 88 ± 6 | 85 ± 7 |
| mAoP (mmHg) | 73 ± 1 | 73 ± 1 | 70 ± 2 | 69 ± 2 | 73 ± 3 | 73 ± 6 |
| LVEDP (mmHg) | 15 ± 0 | 13 ± 1 | 11 ± 1* | 10 ± 1* | 11 ± 1* | 13 ± 1* |
| EDV (ml) | 72 ± 4 | 72 ± 5 | 69 ± 6 | 68 ± 4 | 68 ± 4 | 70 ± 5 |
| ESV (ml) | 54 ± 4 | 54 ± 4 | 47 ± 4* | 45 ± 4* | 44 ± 4* | 49 ± 4* |
| EF (ml) | 26 ± 2 | 26 ± 2 | 31 ± 1* | 34 ± 2* | 35 ± 2* | 30 ± 1* |
| SV (ml) | 19 ± 2 | 18 ± 2 | 22 ± 2 | 23 ± 1 | 23 ± 1 | 20 ± 2 |
| CO (L/min) | 1.59 ± 0.18 | 1.59 ± 0.17 | 1.90 ± 0.19* | 2.06 ± 0.28* | 2.06 ± 0.22* | 1.72 ± 0.17 |
| SVR (dynes-sec-cm$^{-5}$) | 3761 ± 336 | 3774 ± 431 | 2995 ± 213* | 2792 ± 360* | 2886 ± 67* | 3445 ± 310 |

\*= p < 0.05 vs. Baseline

Group II dogs (n=3) received escalating doses of GP-531 tartrate of 3, 10 and 30 µg/kg/min. In this group, there were (Table 3), suggesting a temporal effect in addition to a dose effect.

TABLE 3

Hemodynamic and ventriculographic measures during GP-531 tartrate infusion in Group II dogs (n = 3)

|  | Baseline | Vehicle | GP-531 @ 3 µg/kg/min | GP-531 @ 10 µg/kg/min | GP-531 @ 30 µg/kg/min | Washout |
|---|---|---|---|---|---|---|
| HR (beats/min) | 86 ± 6 | 80 ± 3 | 80 ± 2 | 82 ± 6 | 80 ± 3 | 80 ± 5 |
| mAoP (mmHg) | 68 ± 3 | 71 ± 4 | 70 ± 3 | 65 ± 2 | 69 ± 3 | 66 ± 3 |
| LVEDP (mmHg) | 14 ± 1 | 15 ± 1 | 12 ± 1* | 12 ± 1* | 12 ± 2* | 12 ± 1* |
| EDV (ml) | 59 ± 5 | 62 ± 3 | 62 ± 2 | 58 ± 4 | 57 ± 4 | 59 ± 4 |
| ESV (ml) | 45 ± 2 | 45 ± 2 | 43 ± 2 | 39 ± 3* | 36 ± 3* | 40 ± 2* |
| EF(ml) | 28 ± 0.3 | 28 ± 0.0 | 30 ± 1 | 33 ± 1* | 36 ± 2* | 32 ± 1* |
| SV (ml) | 14 ± 4 | 17 ± 1 | 18 ± 1 | 19 ± 1 | 21 ± 2 | 19 ± 2 |

TABLE 3-continued

Hemodynamic and ventriculographic measures during GP-531 tartrate infusion in Group II dogs (n = 3)

| | Baseline | Vehicle | GP-531 @ 3 μg/kg/min | GP-531 @ 10 μg/kg/min | GP-531 @ 30 μg/kg/min | Washout |
|---|---|---|---|---|---|---|
| CO (L/min) | 1.28 ± 0.39 | 1.39 ± 0.04 | 1.47 ± 0.09 | 1.45 ± 0.06 | 1.64 ± 0.06 | 1.50 ± 0.02 |
| SVR (dynes-sec-cm$^{-5}$) | 5504 ± 2039 | 4106 ± 107 | 3870 ± 366 | 3379 ± 26 | 3388 ± 235 | 3511 ± 176 |

*= p < 0.05 vs. Baseline

Plasma Biomarkers in Groups I and II: In Group I dogs, compared to baseline, plasma levels of NT-Pro-BNP and TnI decreased significantly and to nearly the same magnitude at all doses of GP-531 tartrate administered (Table 4).

In Group II dogs, NT-ProBNP also tended to decrease with escalating doses of GP-531 tartrate but reached significance only at the highest dose of 30 μg/kg/min (Table 4). In this group, TnI also tended to decrease at the highest dose of GP-531 tartrate used but this reduction did not reach statistical significance (Table 4).

TABLE 4

Plasma Levels of NT-ProBNP and TnI in Study Group I and II

| Group I (n = 3) | Baseline | Vehicle | GP-531 @ 30 μg/kg/min | GP-531 @ 100 μg/kg/min | GP-531 @ 300 μg/kg/min | Washout |
|---|---|---|---|---|---|---|
| NT-ProBNP (fmol/ml) | 298 ± 20 | 289 ± 30 | 128 ± 23* | 131 ± 8 * | 121 ± 13* | 204 ± 5* |
| TnI (pg/ml) | 0.42 ± 0.08 | 0.46 ± 0.04 | 0.17 ± 0.03* | 0.13 ± 0.02* | 0.15 ± 0.05* | 0.36 ± 0.03 |

| Group II (n = 3) | Baseline | Vehicle | GP-531 @ 3 μg/kg/min | GP-531 @ 10 μg/kg/min | GP-531 @ 30 μg/kg/min | Washout |
|---|---|---|---|---|---|---|
| NT-ProBNP (fmol/ml) | 252 ± 30 | 241 ± 12 | 225 ± 34 | 155 ± 1 | 123 ± 21* | 179 ± 6 |
| TnI (pg/ml) | 0.41 ± 0.06 | 0.58 ± 0.21 | 0.51 ± 0.05 | 0.50 ± 0.15 | 0.19 ± 0.05 | 0.31 ± 0.05 |

*= p < 0.05 vs. Baseline

Figure 3:
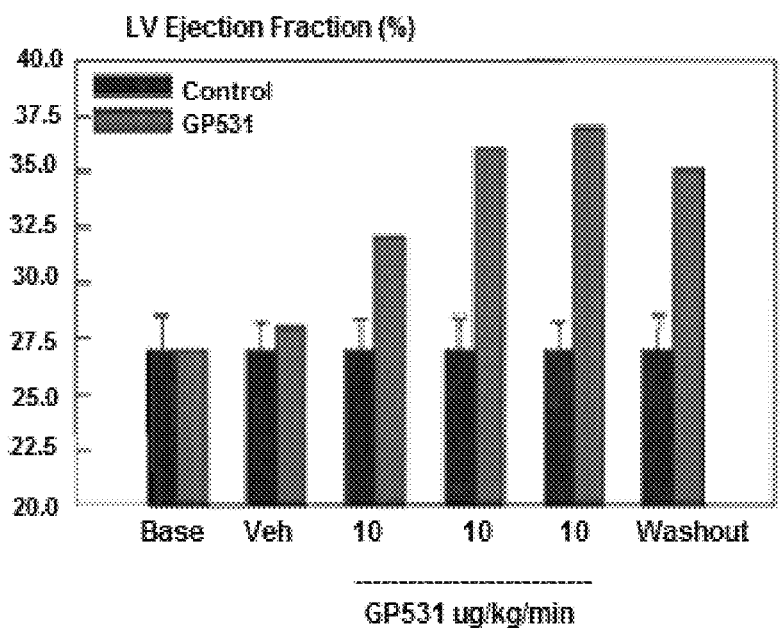
FIG. 3 is a bar graph of LVEF (in %) illustrating that subjects treated with GP-531 tartrate salt as bolus injection (700 μg/kg) followed by 3 hour constant infusion of GP-531 tartrate salt (10 μg/kg/min) showed an increase in LVEF.

Findings in Dogs Treated with Bolus Injection of GP-531 Followed by Constant Infusions In 1 of 8 dogs, GP-531 tartrate was administered as 700 μg/kg bolus followed by a constant infusion of 10 m/kg/min for 3 hours. This infusion protocol resulted in a modest reduction of HR and mAoP and a substantial drop in LVEDP. At the end of 3 hours of infusion, there was a near 10% reduction in EDV, 20% reduction in ESV and a 30% increase in EF (FIG. 3). These improvements appeared to be time dependent. This was accompanied by minimal or modest changes in SV, CO and SVR.

In another 1 of 8 dogs, two GP-531 studies were performed. In one study, GP-531 tartrate was administered as 70 μg/kg bolus followed by a constant infusion of 1.0 μg/kg/min for 4 hours. At this dose, GP-531 had no effects on any of the hemodynamic or ventriculographic measures of LV function. In the second study, GP-531 tartrate was administered as 210 μg/kg bolus followed by a constant infusion of 3.0 μg/kg/min for 4 hours. This infusion protocol resulted in a modest reduction of HR, mAoP and LVEDP. At the end of 4 hours of infusion, there was essentially no change in EDV, a near 20% reduction in ESV and a 44% increase in EF. These improvements appeared to be time dependent. This was accompanied by minimal or modest changes in SV, CO and SVR.

Results indicate that intravenous GP-531 tartrate at doses ranging from 3 to 300 μg/kg/min administered over a period of at least one hour can improve LV systolic function in dogs with advanced chronic heart failure. The improvement in LV systolic function was associated with a reduction in plasma levels of NT-ProBNP and of TnI. These improvements were not associated with any adverse positive chronotropic effects. GP-531 elicited its benefits without inducing hypotension and without triggering de-novo ventricular arrhythmias. The benefits on LV function are likely to be maintained during constant infusions of GP-531 over period of 3 to 4 hours. GP-531's beneficial effects on LV systolic function had not yet peaked at 4 hours.

Example 3

Effects of Acute Intravenous Infusion of GP-531 Tartrate on Left Ventricular Function in Dogs with Advanced Heart Failure: A Single-Dose, 6 Hours Infusion Study Six heart failure dogs described in Example 1 were used. Studies using active drug and placebo were performed in each dog in random order a minimum of one week apart. After baseline hemodynamic, angiographic and echocardiographic measurements, GP-531 tartrate or placebo was administered as a continuous constant intravenous infusion for 6 hours. The dose of GP-531 tartrate was 10 μg/kg/min. Complete hemodynamic, angiographic and echocardiographic measurements were made during baseline, and at 1, 2, 3, 4, 5 and 6 hours after initiating drug infusion. In addition, myocardial oxygen consumption (MVO$_2$) was measured at baseline and 4 and 6 hours after initiating drug or saline infusion. LV pressure-volume relationships (P-V Loops) were also measured at baseline and at 6 hours after initiating drug or saline infusion to assess load independent contractility and relaxation. Venous blood samples were obtained at baseline and hourly thereafter. Blood samples (at least lamp) were centrifuged at 3000 rpm for 10 minutes and plasma withdrawn and placed in cryostorage tubes and stored upright at −20° C. until needed. Venous blood samples were used to evaluate plasma levels of troponin-I and plasma levels of n-terminal pro-brain natriuretic peptide (NT-proBNP).

At the completion of the 6 hour constant infusion study, a secondary study was performed in 3 heart failure dogs to assess the effects of GP-531 in the presence of the non-selective adenosine antagonist 8-p-sulfophenyl theophylline (8-SPT). After baseline hemodynamic and ventriculographic measurements, 8-SPT was administered as 10 mg/kg intravenous bolus followed by 10 mg/kg/hr constant infusion for 3 hours. Infusion of GP-531 tartrate was initiated simultaneously with infusion of 8-SPT at a dose of 10 µg/kg/hr and also maintained for 3 hours. Hemodynamic and ventriculographic measurements were made at 1, 2 and 3 hours.

Study Primary End-Points were: (1) change in LV ejection fraction determined from ventriculography; (2) change in LV end-systolic and end-diastolic volume determined from ventriculography; (3) change in $MVO_2$; and (4) change in the slope of the LV end-systolic and end-diastolic P-V relationship.

All hemodynamic measurements were made during left and right heart catheterizations in anesthetized dogs at each specified study time point. Heart rate (HR), mean aortic pressure (mAoP), LV end-diastolic pressure (LVEDP), stroke volume (SV), cardiac output (CO) and systemic vascular resistance (SVR) were measured at each study time point. Left ventriculograms were performed during cardiac catheterization after completion of the hemodynamic measurements. Left ventriculograms were obtained with the dog placed on its right side and digitally recorded during the injection of 20 ml of contrast material (RENO-M-60 Squibb, Princeton, N.J.). Correction for image magnification was made using a radiopaque grid placed at the level of the LV. LV end-systolic (ESV) and end-diastolic volumes (EDV) were calculated from angiographic silhouettes using the area length method (Dodge H T, et al, *Am J Cardiol.* 1966; 18:10-24.). Premature beats and post-extra-systolic beats were excluded from the analysis. LV ejection fraction (EF) was calculated as the ratio of the difference of end-diastolic and end-systolic volumes to end-diastolic volume times 100, as described above.

Echocardiographic and Doppler studies were performed in all dogs at all specified study time points using a VIVID 7 ultrasound system (General Electric) with a 3.5 MHZ transducer. All echocardiographic measurements were made with the dog placed in the right lateral decubitus position and recorded on a Panasonic 6300 VHS recorder for subsequent off-line analysis. LV fractional area of shortening (FAS), a measure of LV systolic function, was measured from a short axis view at the level of the papillary muscles. LV major and minor semi-axes were measured and used for calculation of LV end-diastolic circumferential wall stress. Wall stress was calculated as follows:

$$EDWS=Pb/h(1-h/2b)(1-hb/2a2)$$

where P is LV end-diastolic pressure, a is LV major semi-axis, b is LV minor semi-axis, and h is LV wall thickness.

Mitral inflow velocity was measured by pulsed-wave Doppler echocardiography to assess LV diastolic function. The velocity waveforms were used to calculate (1) peak mitral flow velocity in early diastole (PE), (2) peak mitral inflow velocity during LA contraction (PA), (3) ratio of PE to PA (PE/PA), (4) time-velocity integral of the mitral inflow velocity waveform representing early filling (Ai), (5) time-velocity integral representing LA contraction (Ai), (6) ratio Ei/Ai, and (7) deceleration time (DCT) of early mitral inflow velocity.

Lead-II of the electrocardiogram was monitored throughout the study and recorded at all specified study time points. Continuous recording of the electrocardiogram was planned only if de-novo ventricular arrhythmias develop. Stopping of drug infusion was planned only if the arrhythmias became life threatening and associated with hemodynamic collapse.

Myocardial oxygen consumption ($MVO_2$) was measured as previously described in detail (Chandler M P, et al., *Circ Res* 91:278-280, 2002). $MVO_2$ measurements were made at baseline, prior to initiating drug infusion and were repeated at the end of 6 hours of drug infusion. Coronary artery blood flow velocity was measured using a Doppler flow velocity catheter (flow wire) placed in the proximal segment of the circumflex coronary artery distal to the first marginal branch. Blood flow was be estimated by calculating the cross-sectional area of the circumflex coronary artery at the site of the catheter-tip using coronary arteriograms. Total LV coronary blood flow was estimated as twice that measured in the circumflex artery. $MVO_2$ was determined as:

$$(MVO_2)=(\text{Total coronary blood flow})\times(\text{aorta to coronary sinus } O_2 \text{ difference})$$

Oxygen content in aorta and coronary sinus blood was measured using an AVOXimeter 1000 (A-VOX Systems, Inc).

Left ventricular Pressure-Volume loops ("P-V loops") were measured using a Millar Instruments MPVS Ultra system in conjunction with a pressure-conductance catheter positioned within the LV cavity. P-V loops generated during a transient balloon occlusion of the inferior Vena Cava were used to assess the slope of the end-systolic pressure volume relation (ESPVR) and the slope of the end-diastolic pressure-volume relation (EDPVR).

Plasma biomarkers were measured in all dogs at all study time points. Troponin I (TnI) was determined in plasma based on the principle of the double antibody sandwich enzyme-linked immunosorbent assay (ELISA) (Hirano, T., et al, *Immunol Today* 1990, 11:443-449) and NT-pro-BNP based on competitive ELISA (Bonow, R. O. *Circulation* 1996, 93:1946-1950). Both biomarkers were assayed using commercially available assay kits. Kits for NT-proBNP and TnI were purchased from ALPCO Diagnostics, Salem, N.H. Using standard curves and software, the concentration of each biomarker was expressed as ng/ml for TnI and fmol/ml for NT-proBNP.

Within group hemodynamic and angiographic data were analyzed using repeated measures analysis of variance (ANOVA) with alpha set at 0.05. If the overall ANOVA was significant, then pairwise comparisons between baseline and drug or placebo dose/time point were performed using the Student-Newman-Keuls test. For this test, a p-value of <0.05 was considered significant. All data are reported as the mean±SEM.

Results: None of the study dogs developed acute decompensation and none died. In addition, none of the dogs developed de-novo ventricular or atrial arrhythmias, sinus tachycardia or hypotension at anytime during either active drug infusions or saline infusion.

Figure 4:
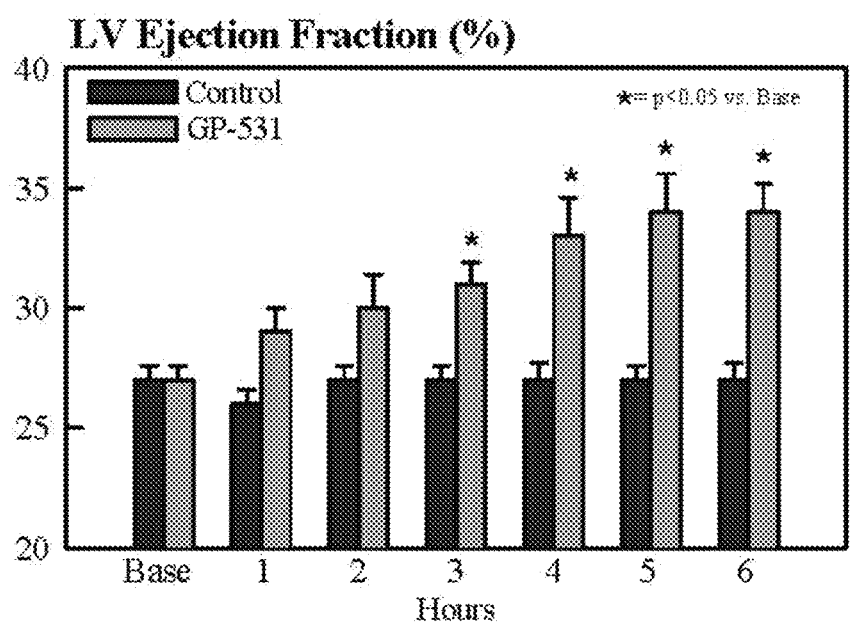
FIG. 4 is a bar graph of LVEF (in %) illustrating that subjects treated with 6 hour constant infusion of GP-531 tartrate salt (10 μg/kg/min) showed an increase in LVEF.

Observations During Saline (Control) Infusion: Saline infusion had no effects on HR, mAoP, LVEDP, SV, CO, and SVR (Table 5). Similarly, saline infusion had no effects on EDV, ESV or EF and had no effect on any of the indexes of LV diastolic function (Table 5, FIG. 4). Saline infusions also had no effects on the slope of the ESPVR and the slope of the EDPVR and no effects on $MVO_2$ (Table 5).

TABLE 5

Hemodynamic, Ventriculographic, and Echocardiographic measurements during saline (control) infusion (n = 6)

|  | Baseline | 1 Hour | 2 Hours | 3 Hours | 4 Hours | 5 Hours | 6 Hours |
|---|---|---|---|---|---|---|---|
| HR (beats/min) | 77 ± 2 | 78 ± 1 | 76 ± 1 | 77 ± 1 | 79 ± 2 | 76 ± 2 | 75 ± 3 |
| mAoP (mmHg) | 81 ± 2 | 76 ± 2 | 74 ± 2 | 76 ± 2 | 76 ± 2 | 77 ± 3 | 75 ± 2 |
| LVEDP (mmHg) | 14 ± 0.4 | 14 ± 0.5 | 14 ± 0.6 | 14 ± 0.6 | 13 ± 0.5 | 13 ± 0.4 | 13 ± 0.5 |
| EDV (ml) | 65 ± 2 | 65 ± 2 | 64 ± 2 | 64 ± 2 | 64 ± 2 | 63 ± 2 | 62 ± 3 |
| ESV (ml) | 47 ± 2 | 48 ± 2 | 47 ± 1 | 47 ± 2 | 47 ± 2 | 46 ± 2 | 46 ± 2 |
| EF (ml) | 27 ± 1 | 26 ± 1 | 27 ± 1 | 27 ± 1 | 27 ± 1 | 27 ± 1 | 27 ± 1 |
| SV (ml) | 17 ± 0.5 | 17 ± 0.6 | 17 ± 0.7 | 17 ± 0.8 | 17 ± 0.7 | 17 ± 0.7 | 17 ± 0.8 |
| CO (L/min) | 1.32 ± 0.05 | 1.33 ± 0.05 | 1.31 ± 0.05 | 1.30 ± 0.06 | 1.34 ± 0.06 | 1.28 ± 0.06 | 1.24 ± 0.07 |
| SVR (dynes-sec-cm$^{-5}$) | 4974 ± 268 | 4585 ± 183 | 4562 ± 231 | 4691 ± 217 | 4582 ± 231 | 4825 ± 195 | 4879 ± 314 |
| FAS (%) | 24 ± 0.5 | 24 ± 0.4 | 24 ± 0.4 | 24 ± 0.4 | 24 ± 0.6 | 24 ± 0.5 | 24 ± 0.5 |
| PE/PA | 1.5 ± 0.04 | 1.5 ± 0.03 | 1.6 ± 0.05 | 1.5 ± 0.03 | 1.5 ± 0.06 | 1.5 ± 0.04 | 1.5 ± 0.06 |
| Ei/Ai | 1.47 ± 0.09 | 1.45 ± 0.05 | 1.52 ± 0.05 | 1.47 ± 0.04 | 1.46 ± 0.08 | 1.44 ± 0.06 | 1.51 ± 0.06 |
| DCT (msec) | 91 ± 3 | 94 ± 3 | 91 ± 3 | 95 ± 4 | 97 ± 5 | 94 ± 3 | 95 ± 4 |
| EDWS (gm/cm$^2$) | 59 ± 5 | 59 ± 2 | 58 ± 3 | 60 ± 5 | 55 ± 5 | 54 ± 4 | 52 ± 4 |
| MVO$_2$ (μmols/min) | 82 ± 9 | — | — | — | 97 ± 24 | — | 84 ± 18 |
| ESPVR (mmHg/ml) | 2.00 ± 0.47 | — | — | — | — | — | 2.36 ± 0.39 |
| EDPVR (mmHg/ml) | 0.410 ± 0.074 | — | — | — | — | — | 0.381 ± 0.059 |

\* = p < 0.05 vs. Baseline

Observations During Infusion of GP-531 tartrate: Infusion of GP-531 tartrate did not evoke any ventricular or atrial arrhythmias. None of the dogs treated with GP-531 developed acute decompensation and none died. Infusion of GP-531 tartrate had no effect on HR or mAoP (Table 6). GP-531 significantly decreased LVEDP in a time-dependent manner reaching significance at 5 hours. GP-531 had no significant effects on peak +dP/dt or peak −dP/dt. It had a modest but statistically significant effect on reducing EDV and significantly decreased ESV and increased EF (FIG. 4) and FAS. These improvements occurred at 1-3 hours after initiating drug infusion. The observed improvements were associated with a significant increase in SV, CO and a decrease in SVR (Table 6). GP-531 significantly increased the slope of the ESPVR. These improvements in LV systolic function occurred in the absence of any changes in MVO$_2$ (Table 6).

Infusion of GP-531 tartrate also had beneficial effects on indexes of LV diastolic function. Both the ratio PE/PA and Ei/Ai increased significantly in a time-dependent fashion (Table 6). DCT increased and EDWS decreased significantly also in a time-dependent fashion. The slope of the EDPVR tended to decrease at 6 hours but the reduction did not reach statistical significance (Table 6).

Figure 5:
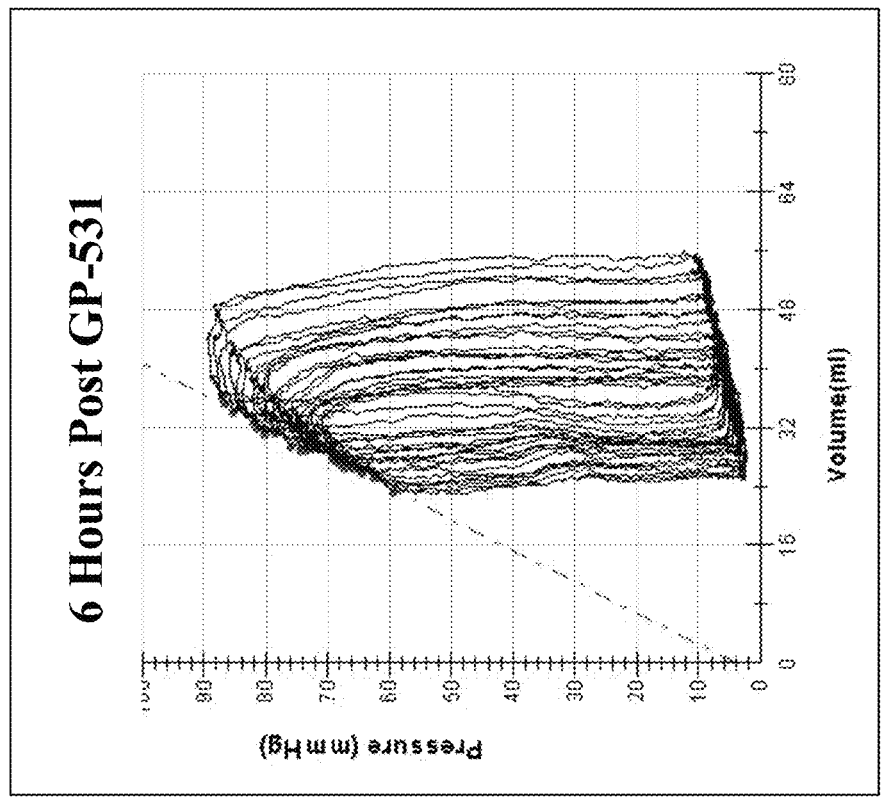
FIG. 5 is a graph of typical Pressure-Volume loops at baseline and 6 hours after administration of GP-531 tartrate salt (10 μg/kg/min).
Figure 5:
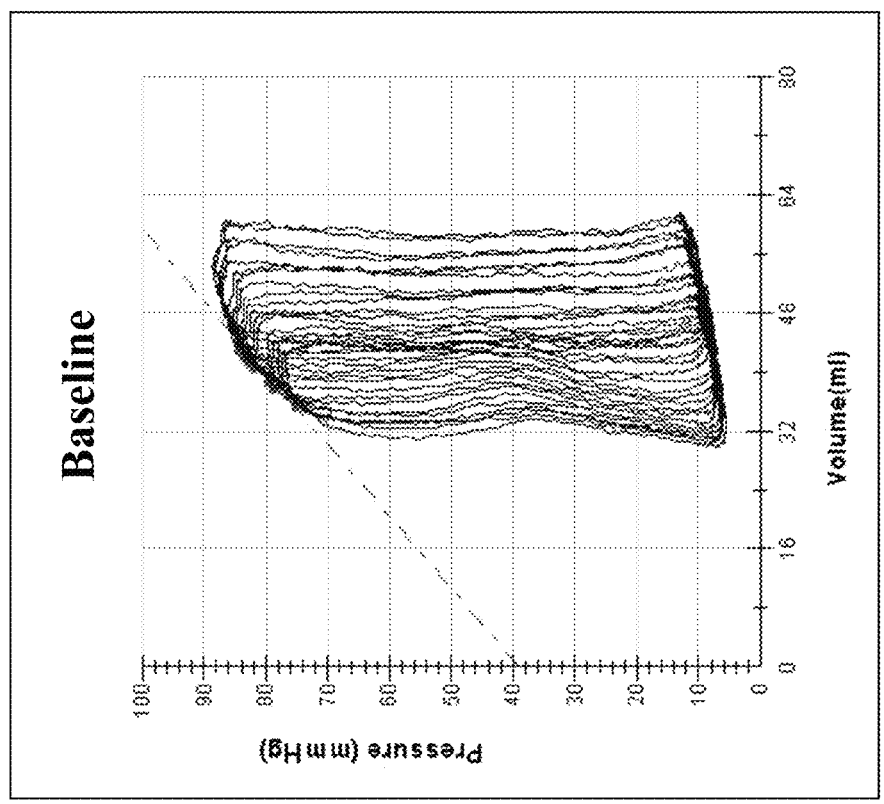

Typical P-V loops at baseline and 6 hours after administration of GP-531 tartrate are shown in FIG. 5. The significant increase in the slope of the end-systolic pressure volume relationship indicate that GP531 improves LV systolic function in a load-independent fashion, that is, it improves intrinsic cardiac contractility. A decrease in the slope of the end-distolic pressure volume relationship indicate that GP531 improves shows a trend in improving LV distolic function in a load-independent fashion, that is it shows a trend in improving intrinsic cardiac relaxation.

TABLE 6

Hemodynamic, Ventriculographic and Echocardiographic Measurements During GP-531 tartrate Infusion (n = 6)

|  | Baseline | 1 Hour | 2 Hours | 3 Hours | 4 Hours | 5 Hours | 6 Hours |
|---|---|---|---|---|---|---|---|
| HR (beats/min) | 79 ± 3 | 78 ± 1 | 78 ± 2 | 79 ± 3 | 80 ± 3 | 79 ± 4 | 81 ± 4 |
| mAoP (mmHg) | 80 ± 3 | 77 ± 3 | 77 ± 3 | 79 ± 3 | 79 ± 3 | 77 ± 2 | 76 ± 3 |
| LVEDP (mmHg) | 13 ± 0.8 | 12 ± 1.1 | 12 ± 0.9 | 12 ± 1.1 | 11 ± 1.2 | 11 ± 1.2 | 10 ± 1.2 |
| EDV (ml) | 65 ± 2 | 64 ± 2* | 63 ± 2* | 63 ± 2* | 63 ± 2* | 62 ± 2* | 62 ± 2* |
| ESV (ml) | 48 ± 2 | 46 ± 2* | 44 ± 2* | 44 ± 2* | 42 ± 2* | 41 ± 2* | 41 ± 2* |
| EF (ml) | 27 ± 1 | 29 ± 1 | 30 ± 1 | 31 ± 1* | 33 ± 2* | 34 ± 2* | 34 ± 1* |
| SV (ml) | 17 ± 0.5 | 18 ± 1.0 | 19 ± 1.2* | 19 ± 0.8* | 21 ± 0.9* | 21 ± 1.1* | 21 ± 0.8* |
| CO (L/min) | 1.36 ± 0.07 | 1.42 ± 0.08 | 1.47 ± 0.11 | 1.53 ± 0.08 | 1.63 ± 0.05* | 1.64 ± 0.07* | 1.69 ± 0.04* |
| SVR (dynes-sec-cm$^{-5}$) | 4766 ± 278 | 4368 ± 248 | 4250 ± 327 | 4157 ± 212* | 3895 ± 168* | 3823 ± 221* | 3571 ± 113* |
| FAS (%) | 24 ± 0.4 | 26 ± 0.8 | 27 ± 1.3* | 29 ± 0.9* | 31 ± 1.5* | 31 ± 1.4* | 32 ± 1.1* |
| PE/PA | 1.5 ± 0.06 | 1.7 ± 0.10 | 1.8 ± 0.10* | 1.9 ± 0.07* | 2.1 ± 0.09* | 2.2 ± 0.05* | 2.2 ± 0.06* |
| Ei/Ai | 1.41 ± 0.10 | 1.78 ± 0.23* | 2.03 ± 0.23* | 2.40 ± 0.29* | 2.51 ± 0.21* | 2.68 ± 0.23* | 2.77 ± 0.23* |
| DCT (msec) | 90 ± 4 | 100 ± 5* | 109 ± 4* | 113 ± 6* | 113 ± 5* | 118 ± 6* | 118 ± 4* |
| EDWS (gm/cm$^2$) | 56 ± 6 | 53 ± 7 | 47 ± 5* | 47 ± 6* | 44 ± 7* | 43 ± 7* | 41 ± 7* |

TABLE 6-continued

Hemodynamic, Ventriculographic and Echocardiographic Measurements During GP-531 tartrate Infusion (n = 6)

|  | Baseline | 1 Hour | 2 Hours | 3 Hours | 4 Hours | 5 Hours | 6 Hours |
|---|---|---|---|---|---|---|---|
| $MVO_2$ (μmols/min) | 104 ± 14 | — | — | — | 114 ± 14 | — | 115 ± 12 |
| ESPVR (mmHg/ml) | 1.86 ± 0.43 | — | — | — | — | — | 2.43 ± 0.35* |
| EDPVR (mmHg/ml) | 0.341 ± 0.028 | — | — | — | — | — | 0.296 ± 0.018 |

*= $p < 0.05$ vs. Baseline

Plasma Biomarkers: Saline (Control) infusions had no effects on plasma levels of NT-proBNP and troponin-I. In contrast, treatment with GP-531 significantly reduced plasma levels of both NT-proBNP and troponin-I (Table 7).

TABLE 7

Plasma Levels of NT-ProBNP and Troponin-I

|  | Baseline | 1 Hour | 2 Hours | 3 Hours | 4 Hours | 5 Hours | 6 Hours |
|---|---|---|---|---|---|---|---|
| Saline Control |  |  |  |  |  |  |  |
| NT-ProBNP (fmol/ml) | 242 ± 13 | 271 ± 14 | 285 ± 14 | 290 ± 14 | 260 ± 12 | 277 ± 12 | 245 ± 12 |
| TnI (pg/ml) | 0.54 ± 0.04 | 0.52 ± 0.04 | 0.56 ± 0.05 | 0.51 ± 0.03 | 0.55 ± 0.04 | 0.54 ± 0.03 | 0.54 ± 0.03 |
| GP-531 (n = 6) |  |  |  |  |  |  |  |
| NT-ProBNP (fmol/ml) | 246 ± 15 | 140 ± 13* | 131 ± 11* | 127 ± 12* | 134 ± 11* | 130 ± 10* | 122 ± 10* |
| TnI (pg/ml) | 0.57 ± 0.03 | 0.57 ± 0.02 | 0.58 ± 0.02 | 0.38 ± 0.03* | 0.43 ± 0.03* | 0.41 ± 0.03* | 0.42 ± 0.06* |

*= $p < 0.05$ vs. Baseline

Observations During 8-SPT Infusion: GP-531 tartrate, when administered simultaneously with 8-SPT, a non-selective adenosine receptor antagonist, had no effects on HR, mAoP, LVEDP, EDV, ESV, EF, SV, CO, and SVR (Table 8).

TABLE 8

Hemodynamic, Ventriculographic and Echocardiographic Measures During GP-531 Infusion Administered Simultaneously with an Infusion of 8-SPT (n = 3)

|  | Baseline | 1 Hour | 2 Hours | 3 Hours |
|---|---|---|---|---|
| HR (beats/min) | 79 ± 3 | 80 ± 4 | 81 ± 5 | 81 ± 6 |
| mAoP (mmHg) | 84 ± 5 | 97 ± 9 | 82 ± 6 | 82 ± 7 |
| LVEDP (mmHg) | 15 ± 0.7 | 16 ± 0.0 | 16 ± 0.3 | 16 ± 0.3 |
| EDV (ml) | 68 ± 3 | 69 ± 3 | 69 ± 3 | 68 ± 3 |
| ESV (ml) | 50 ± 2 | 50 ± 3 | 49 ± 2 | 49 ± 3 |
| EF (ml) | 27 ± 0.3 | 28 ± 0.6 | 28 ± 0.3 | 28 ± 1.0 |
| SV (rnl) | 19 ± 0.9 | 19 ± 0.6 | 19 ± 0.9 | 19 ± 1.0 |
| CO (L/min) | 1.47 ± 0.06 | 1.51 ± 0.08 | 1.57 ± 0.15 | 1.53 ± 0.05 |
| SVR (dynes-sec-$cm^{-5}$) | 4581 ± 209 | 5089 ± 203 | 4191 ± 84 | 4297 ± 253 |

* = $p < 0.05$ vs. Baseline

Results of this study indicate that intravenous GP-531 tartrate administered at a dose of 10 μg/kg/min for 6 hours can improve both LV systolic and diastolic function in dogs with advanced chronic heart failure. The improvement in LV function was associated with a reduction of plasma levels of NT-Pro-BNP and of TnI. These improvements were not associated with any adverse positive chronotropic effects, hypotension or with the development of de-novo ventricular or atrial arrhythmias. The improvement in LV function also occurred in the absence of an increase in myocardial oxygen consumption. The benefits elicited by GP-531 were abolished when administered in conjunction with 8-SPT, a non-selective adenosine receptor antagonist suggesting that preservation of adenosine receptors binding helps provide for the accrued benefits.

Example 4

GP531-di-O-pivaloyl Prodrug

To enhance the oral bioavailability of GP531 (~10% in man) a evaluation of a di-O-pivaloyl prodrug was undertaken in the rat and the monkey.

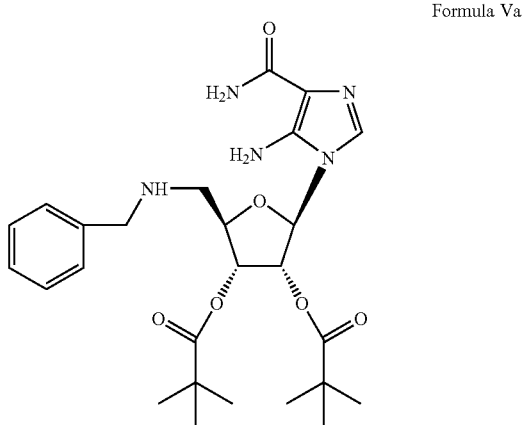 [SMILES: CC(C)(C)C(=O)O[C@@H]1[C@H](OC(=O)C(C)(C)C)[C@@H](CNCc2ccccc2)O[C@H]1n1cnc(C(N)=O)c1N]

Formula Va

Administering a better absorbed more lipophilic prodrug, which is subsequently hydrolysed to GP531, achieves an increase in the systemic availability of GP531. GP531 has an unfavorable octanol: water partition coefficient (log P=−0.91) for absorption while the prodrug Formula Va exhibited a very significant increase in lipophilicity (log P=3.31).

Figure 6:
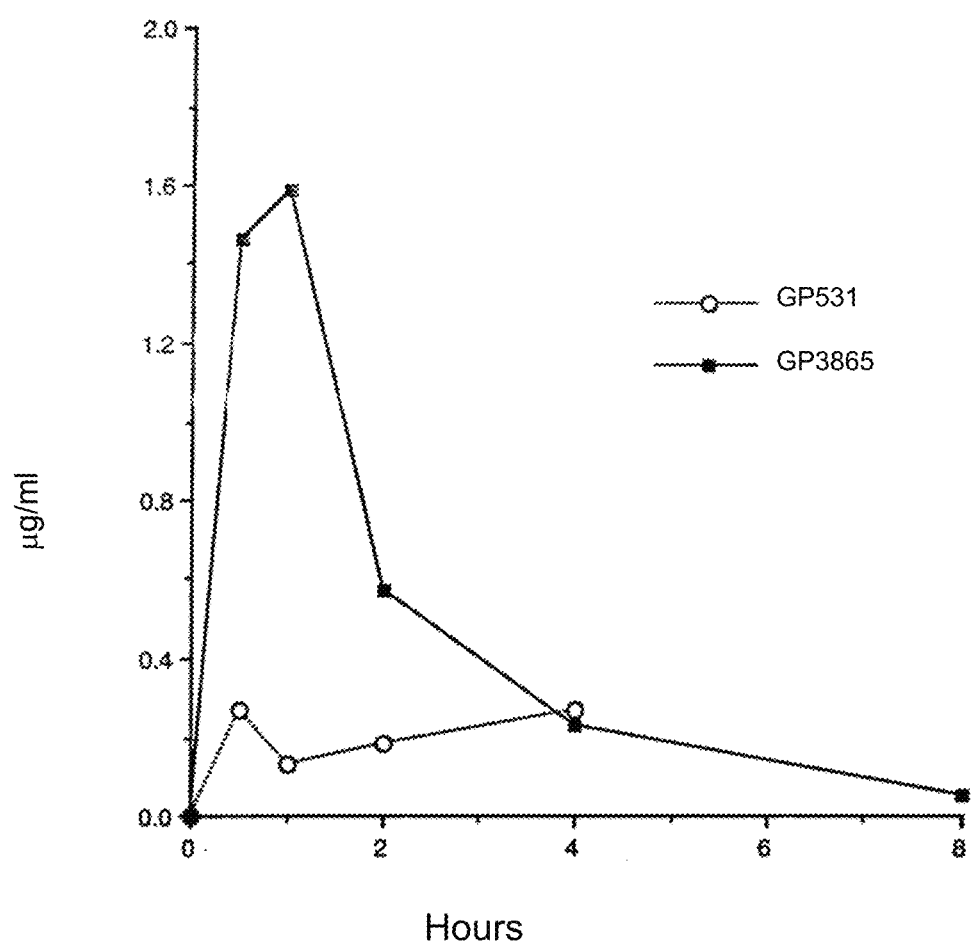
FIG. 6 is a graph of the mean plasma concentrations of GP-531 in the rat following oral administration of equimolar doses (20 mg/kg) of GP-531 tartrate salt and the compound of Formula Va hydrochloride salt.

Two separate studies were conducted in the rat using the free base and/or the water soluble hydrochloride salt of Formula Va. In the first study, equimolar doses of GP531 (20 mg/kg) were administered orally in aqueous solution to separate groups (n=3) of rats as GP531 tartrate or Formula Va hydrochloride. Plasma concentrations of GP531 were determined in both groups of animals and the mean data are presented in FIG. 6. It can be seen that there was a significant increase in both the $C_{max}$ and AUC of GP531 following administration of the prodrug. $C_{max}$ increased 6-fold and AUC over 0-4 hr increased 4-fold. In a subsequent study, using the same equimolar doses of GP531 tartrate and prodrug, the relative bioavailability of GP531 was estimated in a group of rats (n=4) by comparison of the amount of GP531 excreted in urine after dosing. (Previous studies have shown that GP531 is not metabolized and is cleared almost entirely intact in urine.) The urinary excretion data that there was an approximately 3-fold increase in the excretion of GP531 following administration of the prodrug which supported the previously observed increase in bioavailability based on plasma AUC data. The urinary excretion data indicated that the absolute oral bioavailability of GP531 following administration of the prodrug was about 40%. There was no significant difference in GP531 bioavailability regardless of whether the free base or hydrochloride salt of the prodrug was dosed.

Figure 7:
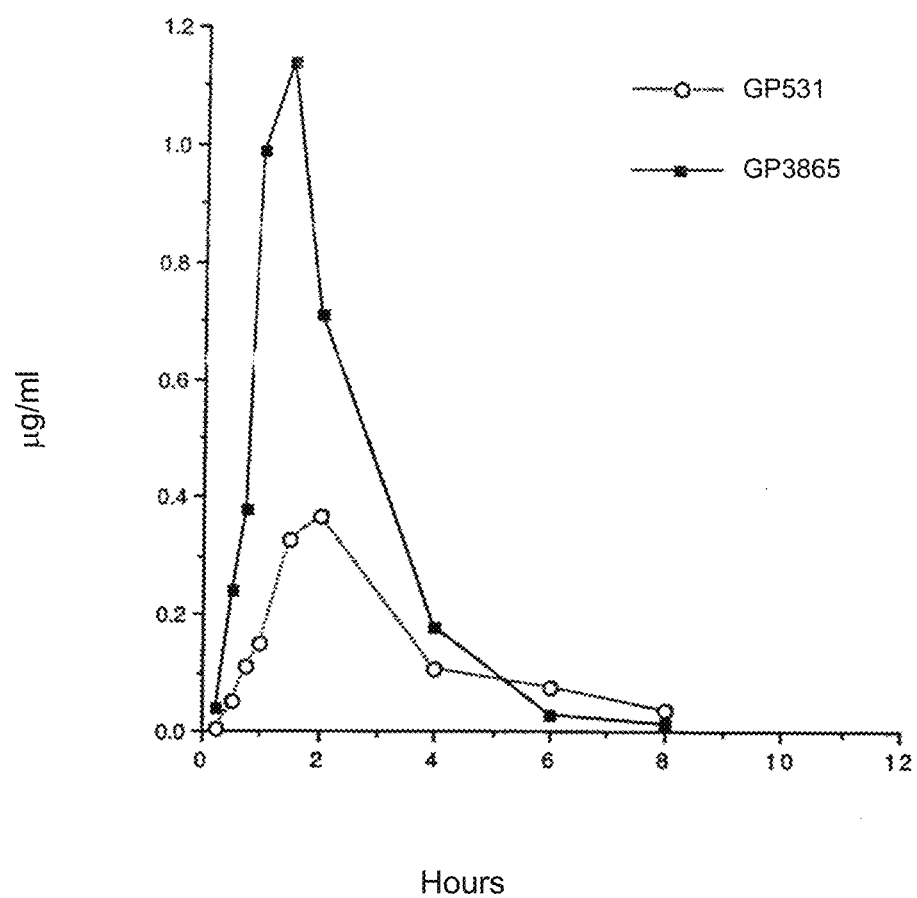
FIG. 7 is a graph of the mean plasma concentrations of GP-531 in the monkey following oral administration of equimolar doses (20 mg/kg) of GP-531 tartrate salt and the compound of Formula Va hydrochloride salt.

A preliminary study was also conducted in the monkey (n=4) using Formula Va hydrochloride as the prodrug. The resulting plasma level data for GP531 were compared to previous data on file from a separate group of monkeys that had been dosed orally with an equimolar dose of GP531 tartrate. It can be seen in FIG. 7 that there was a 3-fold increase in the mean max and an over 2-fold increase in AUC over 0-8 hr following administration of the prodrug.

Example 5

Clinical Trial

A multi-center, randomized, double blind, placebo controlled, Phase 2 safety and dose-escalation study to assess the safety, tolerability, hemodynamic and echocardiographic effects of GP531 tartrate, in patients hospitalized with worsening heart failure, i.e. acute heart failure patients.

A total of 150 subjects are randomized in each of 5 cohorts, placebo (normal saline and 0.1 mg/mL sodium metabisulfite) and GP531 tartrate (100 mg/mL in saline and 0.1 mg/mL sodium metabisulfite), starting at a dose of 2 μg/kg/min, followed by escalating doses of 6 μg/kg/min, 18 μg/kg/min, 54 μg/kg/min and 100 μg/kg/min administered as an IV infusion over approximately 24 hours. 30 subjects are randomized to placebo and 120 to treatment.

Efficacy is assessed by:
 a. Comparison of changes in hemodynamic measurements between treatment and control groups by echocardiography from baseline include:
  1) Left ventricular function;
  2) Left ventricular diastolic function and hemodynamics;
  3) Pulmonary artery systolic pressure;
  4) Valvular function assessed by mitral and tricuspid regurgitation grade
 b. Comparison between treatment and control groups in signs and symptoms to include:
  1) Dyspnea assessed by a self-administered, 7-point Likert dyspnea scale at ~24 h
  2) Changes in clinical status assessed by self-administered visual analog scale (VAS) from baseline to ~24 h
  3) Changes in body weight from baseline to approximately 24 h, 48 h, 72 h, 96 h (or on discharge if before 96 h)
 c. Comparison of changes between treatment and control groups in BNP and Troponin I from baseline to 24 h, 48 h, 72 h, 96 h (or on discharge if before 96 h) and 8 days post randomization.
 d. Comparison of differences between treatment and control groups in incidence rates at 30 days and 60 days post randomization of:
  1) rehospitalizations due to heart failure
  2) rehospitalization due to cardiovascular events
  3) mortality due to cardiovascular events
  4) All-cause mortality Generally, administering to an acute heart failure patient in need thereof an AICA riboside analog of Formula I, alternately of Formula II, III, IV or V, in particular GP531 or a pharmaceutically acceptable salt or prodrug thereof accomplishes one or more of:
 (a) prolonging time to second or third hospitalization due to heart failure;
 (b) reducing the number of days a patient spends in the hospital for heart failure;
 (c) reducing the number of hospital admissions for heart failure;
 (d) reducing the number of hospital admissions for cardiovascular events;
 (e) reducing mortality due to heart failure;
 (f) reducing mortality due to cardiovascular events;
 (g) improving cardiac output;
 (h) improving diastolic function;
 (i) improving left ventricular ejection fraction;
 (j) decreasing levels of B-type natriuretic peptide;
 (k) decreasing levels of cardiac troponin; and
 (l) reducing dyspnea, resulting from a reduction in congestion.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed:

1. A method of treating acute decompensated heart failure in a patient in need thereof, comprising administering to the patient an effective amount of a compound of Formula V:

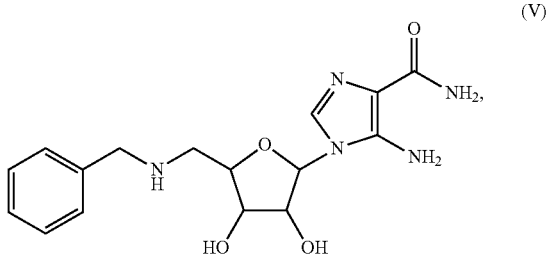 [SMILES: NC(=O)c1ncn(C2OC(CNCc3ccccc3)C(O)C2O)c1N]

or a pharmaceutically acceptable salt thereof.

2. The method of claim 1, wherein the patient has non-ischemic cardiomyopathy.

3. The method of claim 1, whereby the administering step results in an improvement in global cardiac function in the patient.

4. The method of claim 1, wherein global cardiac function comprises left ventricular function, left ventricular systolic function, left ventricular diastolic function, and/or efficiency of cardiac contraction.

5. The method of claim 4, wherein left ventricular systolic function comprises one or more of left ventricular ejection fraction, cardiac output, or stroke volume.

6. The method of claim 1, whereby the administering step does not produce a statistically significant increase in any one or more of blood pressure, myocardial oxygen consumption, or heart rate in the patient.

7. The method of claim 1, whereby the administering step does not cause hypotension, tachycardia, or arrhythmia in the patient.

8. The method of claim 1, whereby the administering step causes a reduction in plasma levels of NT-Pro-BNP and TnI in the patient.

9. The method of claim 1, wherein the patient has a left ventricular ejection fraction of less than 35% prior to the administering step.

10. The method of claim 1, wherein the patient has a left ventricular ejection fraction of greater than 40% prior to the administering step.

11. The method of claim 1, wherein the compound of Formula V or a pharmaceutically acceptable salt thereof is:

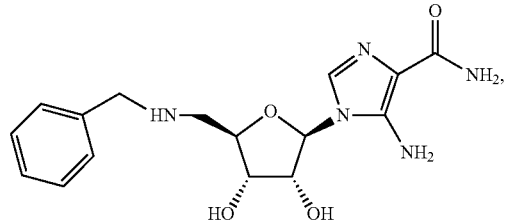 [SMILES: NC(=O)c1ncn([C@@H]2O[C@H](CNCc3ccccc3)[C@@H](O)[C@H]2O)c1N]

or a pharmaceutically acceptable salt thereof.

12. The method of claim 1, wherein the compound of Formula V or pharmaceutically acceptable salt thereof is administered for between about 1 hour and about 24 hours.

13. The method of claim 1, wherein the administering step is not accompanied by administration of an increased dose of a diuretic, an inotrope, or a vasodilator to the patient.

14. The method of claim 1, wherein the compound of Formula V or pharmaceutically acceptable salt thereof is administered at a rate in the range of about 3 µg/kg/min to about 300 µg/kg/min.

15. The method of claim 14, wherein the administration rate is less than 100 µg/kg/min.

16. A method of treating decompensation of cardiac function associated with acute decompensated heart failure in a patient in need thereof, comprising administering to the patient an effective amount of a compound of Formula V:

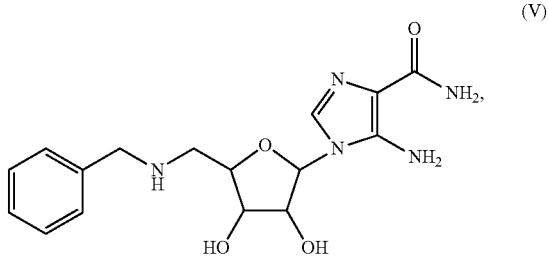 [SMILES: NC(=O)c1ncn(C2OC(CNCc3ccccc3)C(O)C2O)c1N]

or a pharmaceutically acceptable salt thereof.

17. The method of claim 16, wherein an improvement in global cardiac function of the patient occurs within three hours of initiation of the administering step.

18. The method of claim 16, wherein an improvement in global cardiac function of the patient occurs within one hour of initiation of the administering step.

19. A method of improving global cardiac function in a patient with acute decompensated heart failure, comprising administering to the patient an effective amount of a compound of Formula V:

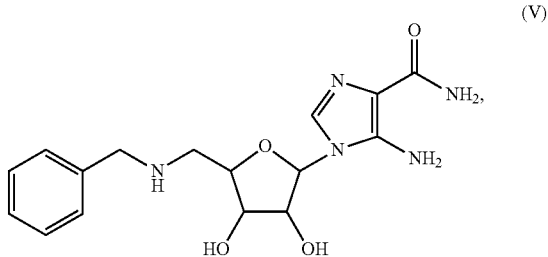 [SMILES: NC(=O)c1ncn(C2OC(CNCc3ccccc3)C(O)C2O)c1N]

or a pharmaceutically acceptable salt thereof.

20. The method of claim 19, wherein improving global cardiac function comprises improving left ventricular function.

21. The method of claim 19, wherein left ventricular function comprises left ventricular systolic function and left ventricular diastolic function.

22. The method of claim 21, wherein left ventricular systolic function comprises one or more of left ventricular ejection fraction, cardiac output, or stroke volume.

23. The method of claim 19, wherein improving global cardiac function comprises improving efficiency of cardiac contraction in the patient.

24. The method of claim 19, whereby the administering step does not produce a statistically significant increase in any one or more of blood pressure, myocardial oxygen consumption, or heart rate in the patient.

25. The method of claim 19, whereby the administering step does not cause hypotension, tachycardia, or arrhythmia in the patient.

26. The method of claim 19, whereby the administering step causes a reduction in plasma levels of NT-Pro-BNP and TnI in the patient.

27. The method of claim 19, wherein the patient has non-ischemic cardiomyopathy.

28. The method of claim 19, wherein the patient has a left ventricular ejection fraction of less than 35% prior to the administering step.

29. The method of claim 19, wherein the patient has a left ventricular ejection fraction of greater than 40% prior to the administering step.

30. The method of claim 19, wherein the improvement in global cardiac function occurs within six hours of initiation of the administering step.

31. The method of claim 30, wherein the improvement in global cardiac function occurs within three hours of initiation of the administering step.

32. The method of claim 30, wherein the improvement in global cardiac function occurs within one hour of initiation of the administering step.

33. The method of claim 19, wherein the compound of Formula V or a pharmaceutically acceptable salt thereof is:

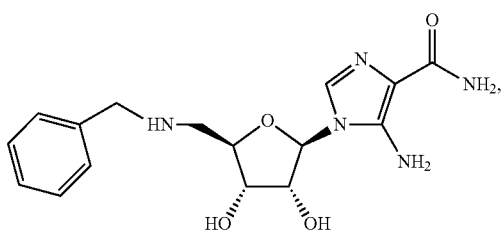 [SMILES: NC(=O)c1ncn([C@@H]2O[C@H](CNCc3ccccc3)[C@@H](O)[C@H]2O)c1N]

or a pharmaceutically acceptable salt thereof.

* * * * *